US007521182B2

(12) United States Patent
Tenson et al.

(10) Patent No.: US 7,521,182 B2
(45) Date of Patent: Apr. 21, 2009

(54) SELECTION SYSTEM CONTAINING NON-ANTIBIOTIC RESISTANCE SELECTION MARKER

(75) Inventors: Tanel Tenson, Tartu (EE); Silja Laht, Tartu (EE); Maarja Ado-Jaan, Tartu region (EE); Andres Männik, Tartu (EE); Urve Toots, Tartu (EE); Mart Ustav, Tartu (EE)

(73) Assignee: FIT Biotech OY, Tampere (SE)

( * ) Notice: Subject to any disclaimer, the term of this patent is extended or adjusted under 35 U.S.C. 154(b) by 1 day.

(21) Appl. No.: 10/531,870

(22) PCT Filed: Sep. 15, 2004

(86) PCT No.: PCT/FI2004/000540

§ 371 (c)(1),
(2), (4) Date: Apr. 19, 2005

(87) PCT Pub. No.: WO2005/026364

PCT Pub. Date: Mar. 24, 2005

(65) Prior Publication Data

US 2007/0036822 A1 Feb. 15, 2007

(30) Foreign Application Priority Data

Sep. 15, 2003 (FI) .................................. 20031319

(51) Int. Cl.
*C12Q 1/02* (2006.01)
*C12N 1/20* (2006.01)
*C12N 1/21* (2006.01)
*C12N 15/70* (2006.01)

(52) U.S. Cl. .................. 435/6; 435/252.33; 435/252.8; 435/320.1

(58) Field of Classification Search ........................ None
See application file for complete search history.

(56) References Cited

U.S. PATENT DOCUMENTS

| | | | |
|---|---|---|---|
| 5,824,485 | A | 10/1998 | Thompson et al. |
| 5,843,760 | A | 12/1998 | Zhang et al. |
| 5,876,931 | A | 3/1999 | Holden |
| 6,030,807 | A | 2/2000 | De Lencastre et al. |
| 6,162,433 | A | 12/2000 | Khan et al. |
| 6,368,793 | B1 | 4/2002 | Hoch et al. |
| 6,479,279 | B2 | 11/2002 | Ustav |
| 6,500,647 | B1 | 12/2002 | Jung et al. |
| 6,803,210 | B2 | 10/2004 | Better |

FOREIGN PATENT DOCUMENTS

WO    WO 98/07876    2/1998

OTHER PUBLICATIONS

Andersson et al., Purification and preliminary X-ray crystallographic studies of recombinant L-ribulose-5-phosphate 4-epimerase from *Escherichia coli*, *Protein Science*, 1995, vol. 4, pp. 1648-1650, Oxford University Press, Oxford, England.

Ariza et al., "A method for selection of forward mutations in *supF* gene carried by shuttle-vector plasmids," *Carcinogenesis*, 1993, vol. 14, n. 2, pp. 303-305, Oxford University Press, Oxford, England.

Datsenko et al., "One-step inactivation of chromosomal genes in *Escherichia coli* K-12 using PCR products," *PNAS*, 2000, vol. 97, n. 12, pp. 6640-6645, National Academy of Sciences, Washington, D.C.

Herrero et al., "Transposon Vectors Containing Non-Antibiotic Resistance Selection Markers for Cloning and Stable Chromosomal Insertion of Foreign Genes in Gram-Negative Bacteria," *Journal of Bacteriology*, 1990, vol. 172, n. 11, pp. 6557-6567, American Society for Microbiology, Washington, D.C.

Englesberg et al., L-Arabinose-sensitive, L-Ribulose 5-Phosphate 4-Epimerase-Deficient Mutants of *Escherichia coli*, *Journal of Bacteriology*, 1962, vol. 84, pp. 137-146, American Society for Microbiology, Washington, D.C.

Wang et al., "Cloning of Genese That Suppress an *Escherichia coli* K-12 Alanine Auxotroph When Present In Multicopy Plasmids," *Journal of Bacteriology*, 1987, vol. 169, n. 12, pp. 5610-5614, American Society for Microbiology, Washington, D.C.

Yew et al., "Utilization of L-Ascorbate by *Escherichia coli* K-12: Assignments of Functions to Products of the *yif-sga* and *yia-sgb* OPerons," *Journal of Bacteriology*, 2002, vol. 184, n. 1, pp. 302-306, American Society for Microbiology, Washington, D.C.

Levy, "Factors impacting on the problem of antibiotic resistance," *Journal of Antimicrobial Chemotherapy*, 2002, vol. 49, pp. 25-30, The British Society for Antimicrobial Chemotherapy, London, England.

Engelberg-Kulka et al., "Addiction Modules and Programmed Cell Death and Antideath in Bacterial Cultures," *Annual Review of Microbiology*, 1999, vol. 53, pp. 43-70.

Silver et al., "Bacterial Heavy Metal Resistance: New Surprises," *Annual Review of Microbiology*, 1996, vol. 50, pp. 753-789.

(Continued)

*Primary Examiner*—Nancy Vogel
(74) *Attorney, Agent, or Firm*—Buchanan Ingersoll & Rooney, PC

(57) ABSTRACT

A selection system free of antibiotic resistance genes, which is based on the use of an araD gene as a selection marker carried on a vector which is inserted in a bacterial strain deficient of the araD gene. The araD gene from *E. coli* encodes the L-ribulose-5-phosphate-4-epimerase. A method of selecting the cells transformed with a plasmid, which contains the araD gene. The non-antibiotic selection marker makes the system suitable for producing therapeutics. The araD gene is not essential for growth of the host but manipulation of it affects the growth under certain selective conditions. Deletion of araD leads to accumulation of substance which is toxic to the host but not to humans. The araD gene is relatively small and therefore a small plasmid may be constructed, which requires less energy for replication, and leads to increased growth rate and yield.

34 Claims, 26 Drawing Sheets

OTHER PUBLICATIONS

Ilves et al., "Long-Term Episomal Maintenance of Bovine Papillomavirus Type 1 Plasmids is Determined by Attachment to Host Chromosomes, Which is Mediated by the Viral E2 Protein and its Binding Sites", Journal of Virology, vol. 73, No. 5, pp. 4404-4412, May 1999.

Van Craenenbroeck et al., "Episomal Vectors for Gene Expression in Mammalian Cells", Eur. J. Biochem. vol. 267, pp. 5665-5678, 2000.

Collings et al., "Humoral and Cellular Immune Responses to HIV-1 NEF in Mice DNA-Immunized with Non-replicating or Self-replicating Expression Vectors", Vaccine, vol. 18, pp. 460-467, 2000.

Bowers et al., "Bacterial Expression System with Tightly Regulated Gene Expression and Plasmid Copy Number", Gene, 2004, vol. 340, pp. 11-18.

Cribbs et al., "L-Arabinose Negative Mutants of the L-Ribulokinase Structural Gene Affecting the Levels of L-Aravinose Isomerase in *Escherichia coli*", Genetics, Jan. 1964, vol. 49, pp. 95-108.

Khlebnikov et al., "Regulatable Arabinose-Inducible Gene Expression System with Consistent Control in All Cells of a Culture", Journal of Bacteriology, Dec. 2000, vol. 182, No. 24, pp. 7029-7034.

Khlebnikov et al., "Modulation of Gene Expression from the Arabinose-Inducible araBAD Promoter", Journal of Industrial Microbiology & Biotechnology, 2002, vol. 29, pp. 34-37.

```
  1 GGATCCGACC GGCAACGGTA CAGATCCGAC CGGCAACGGT ACAGATCCGA
       <<...................10E2BS....................<

51 CCGGCAACGG TCAGATCCGA CCGGCAACGG TACAGATCCG ACCGGCAACG
       <.....................10E2BS......................<

101 GTACAGATCC GACCGGCAAC GGTACAGATC CGACCGGCAA CGGTACAGAT
       <.....................10E2BS......................<
                >>deletion start in clone 14

151 CCGACCGGCA ACGGTACAGA TCCGACCGGC AACGGTACAG ATCCGACCGG
       <.....................10E2BS......................<

201 CAACGGTACA GATCCCCCTA GCGAATTGAC TAGTTCTCAT GTTTGACAGC
       <..10E2BS.<<                       >>...promoter....>
deletion end in #14>>

T→mutation in #2A
                                          ↑
251 TTATCATCGA TAAGCTTTAA TGCGGTAGTT TAGCACGAAG GAGTCAACAT
       >............promoter............>>   >>RBS.>>

T→STOP in clone 13             araD >>
                ↑
301 GTTAGAAGAT CTCAAACGCC AGGTATTAGA AGCCAACCTG GCGCTGCCAA
     M  L  E  D   L  K  R   Q  V  L   E  A  N  L   A  L  P
       >.....................araD........................>

351 AACACAACCT GGTCACGCTC ACATGGGGCA ACGTCAGCGC CGTTGATCGC
     K  H  N  L   V  T  L   T  W  G   N  V  S  A   V  D  R
       >.....................araD........................>

401 GAGCGCGGCG TCTTTGTGAT CAAACCTTCC GGCGTCGATT ACAGCGTCAT
     E  R  G   V  F  V   I  K  P  S   G  V  D  Y   S  V
       >.....................araD........................>

451 GACCGCTGAC GATATGGTCG TGGTTAGCAT CGAAACCGGT GAAGTGGTTG
     M  T  A  D   D  M  V   V  V  S   I  E  T  G   E  V  V
       >.....................araD........................>
```

Figure 13

```
501  AAGGTACGAA AAAGCCCTCC TCCGACACGC CAACTCACCG GCTGCTCTAT
      E  G  T   K  K  P  S   S  D  T   P  T  H   R  L  L  Y
     >..................araD........................>

551  CAGGCATTCC CCTCCATTGG CGGCATTGTG CATACGCACT CGCGCCACGC
       Q  A  F   P  S  I   G  G  I  V   H  T  H   S  R  H
     >..................araD........................>

601  CACCATCTGG GCGCAGGCGG GTCAGTCGAT TCCAGCAACC GGCACCACCC
      A  T  I  W   A  Q  A   G  Q  S   I  P  A  T   G  T  T
     >..................araD........................>

651  ACGCCGACTA TTTCTACGGC ACCATTCCCT GCACCCGCAA AATGACCGAC
      H  A  D   Y  F  Y  G   T  I  P   C  T  R   K  M  T  D
     >..................araD........................>

701  GCAGAAATCA ACGGCGAATA TGAGTGGGAA ACCGGTAACG TCATCGTAGA
       A  E  I   N  G  E   Y  E  W  E   T  G  N   V  I  V
     >..................araD........................>

751  AACCTTTGAA AAACAGGGTA TCGATGCAGC GCAAATGCCC GGCGTTCTGG
       E  T  F  E   K  Q  G   I  D  A   A  Q  M  P   G  V  L
     >..................araD........................>

801  TCCATTCCCA CGGCCCGTTT GCATGGGGCA AAAATGCCGA AGATGCGGTG
       V  H  S   H  G  P  F   A  W  G   K  N  A   E  D  A  V
     >..................araD........................>

851  CATAACGCCA TCGTGCTGGA AGAGGTCGCT TATATGGGGA TATTCTGCCG
        H  N  A   I  V  L   E  E  V  A   Y  M  G   I  F  C
     >..................araD........................>

901  TCAGTTAGCG CCGCAGTTAC CGGATATGCA GCAAACGCTG CTGGATAAAC
       R  Q  L  A   P  Q  L   P  D  M   Q  Q  T  L   L  D  K
     >..................araD........................>

951  ACTATCTGCG TAAGCATGGC GCGAAGGCAT ATTACGGGCA GTAATGACAG
       H  Y  L   R  K  H  G   A  K  A   Y  Y  G   Q  -
     >..................araD...................>>
                                              terminator >>

1001 CCCGCCTAAT GAGCGGGCTT TTTTTTCCAT

>........terminator.......>>
```

Figure 13 (cont.)

```
1400    ATAAACTGAA CTATCGCGGT TCTTTCCTGA TTGAGATGTG GACCGAAAAA
                   >........................sgbU........................>

1450    GCCAAAGAGC CGGTGCTGGA GATTATTCAG GCGCGGCGTT GGATTGAAGC
        >........................sgbU........................>

1500    GCGTATGCAG GAGGCTGGAT TTATATGTTA GAGCAACTGA AAGCCGACGT
                                         M  L  E  Q  L  K  A  D
        >.............sgbU.............>>
                                       >>..........sgbE............>

1550    GCTGGCGGCG AATCTGGCGC TTCCCGCTCA CCATCTGGTG ACGTTCACCT
        V  L  A  A  N  L  A  L  P  A  H  H  L  V  T  F  T
        >........................sgbE........................>
```

```
1600  GGGGCAATGT CAGCGCGGTA GACGAAACGC GGCAATGGAT GGTAATCAAA
       W  G  N   V  S  A  V   D  E  T   R  Q  W   M  V  I  K
      >.....................sgbE........................>

1650  CCTTCCGGCG TCGAGTACGA CGTGATGACC GCCGACGATA TGGTGGTGGT
        P  S  G   V  E  Y   D  V  M  T   A  D  D   M  V  V
      >.....................sgbE........................>

1700  TGAGATAGCC AGCGGTAAGG TGGTGGAAGG CAGCAAAAAA CCCTCTTCCG
       V  E  I  A   S  G  K   V  V   E  G   S  K  K   P  S  S
      >.....................sgbE........................>

1750  ATACACCAAC GCATCTGGCG CTCTACCGTC GCTATGCCGA AATTGGCGGT
       D  T  P   T  H  L  A   L  Y  R   R  Y  A   E  I  G  G
      >.....................sgbE........................>

1800  ATTGTGCATA CCCACTCGCG CCACGCCACC ATCTGGTCAC AGGCCGGGCT
         I  V  H   T  H  S   R  H  A  T   I  W  S   Q  A  G
      >.....................sgbE........................>

1850  GGATCTCCCC GCCTGGGGCA CCACCCACGC CGATTATTTT TACGGTGCCA
       L  D  L  P   A  W  G   T  T  H   A  D  Y  F   Y  G  A
      >.....................sgbE........................>

1900  TCCCCTGCAC GCGACAGATG ACCGCAGAGG AGATTAACGG CGAATATGAA
         I  P  C   T  R  Q  M   T  A  E   E  I  N   G  E  Y  E
      >.....................sgbE........................>

1950  TATCAGACCG GCGAAGTGAT CATTGAAACC TTCGAAGAAC GTGGCAGGAG
         Y  Q  T   G  E  V   I  I  E  T   F  E  E   R  G  R
      >.....................sgbE........................>

2000  TCCGGCACAA ATCCCGGCGG TGCTGGTGCA TTCTCACGGC CCGTTCGCAT
       S  P  A  Q   I  P  A   V  L  V   H  S  H  G   P  F  A
      >.....................sgbE........................>

2050  GGGGTAAAAA CGCCGCCGAT GCCGTGCATA ACGCCGTAGT ACTCGAAGAA
        W  G  K   N  A  A  D   A  V  H   N  A  V   L  E  E
      >.....................sgbE........................>

2100  TGCGCCTATA TGGGTCTATT CTCGCGCCAG CTTGCGCCGC AGCTCCCTGC
         C  A  Y   M  G  L   F  S  R  Q   L  A  P   Q  L  P
      >.....................sgbE........................>

2150  GATGCAAAAC GAACTGCTGG ATAAGCACTA CCTGCGTAAG CATGGGGCCA
       A  M  Q  N   E  L  L   D  K  H   Y  L  R  K   H  G  A
      >.....................sgbE........................>

2200  ATGCCTATTA CGGGCAGTAA TCCCTCACGC CGGGGCTTCA TCGCCCCGGC
        N  A  Y  Y   G  Q  -
      >........sgbE........>>

2250  ACTACGAATT GATATGTTCC TTGCTGTAAC GCCGCTTCCA CGCTGCTGGC

(2792 bps)

```
1400    CGGGCCGTAC CTGATTGAGA TGTGGAGCGA AACGGCGGAA GACCCGGCGG
        >..................sgaU.........................>

1450    CAGAAGTGGC GAAAGCGCGT GATTGGGTGA AAGCGCGCAT GGCGAAAGCG
        >..................sgaU.........................>

1500    GGCATGGTGG AGGCGGCATA ATGCAAAAGC TAAAACAGCA GGTATTTGAA
                                M   Q   K   L   K   Q   Q   V   F   E
        >........sgaU........>>
                             >>............UlaF.............>

1550    GCCAACATGG AGCTGCCGCG CTACGGGCTG GTGACCTTTA CCTGGGGCAA
         A   N   M   E   L   P   R   Y   G   L   V   T   F   T   W   G
        >.........................UlaF.........................>
```

```
1600  CGTCAGCGCT ATCGACCGCG AACGCGGGCT GGTGGTGATC AAGCCCAGCG
       N  V  S  A  I  D  R  E  R  G  L  V  V  I  K  P  S
      >..................UlaF..........................>

1650  GCGTTGCCTA CGAAACCATG AAAGCGGCCG ATATGGTGGT GGTTGATATG
       G  V  A  Y  E  T  M  K  A  A  D  M  V  V  D  M
      >..................UlaF..........................>

1700  AGCGGCAAGG TGGTGGAAGG GGAGTATCGC CCATCTTCCG ACACTGCGAC
       S  G  K  V  V  E  G  E  Y  R  P  S  S  D  T  A
      >..................UlaF..........................>

1750  GCATCTCGAA CTCTACCGTC GTTACCCGTC GCTTGGTGGC ATTGTCCATA
       T  H  L  E  L  Y  R  R  Y  P  S  L  G  G  I  V  H
      >..................UlaF..........................>

1800  CCCACTCCAC TCATGCCACC GCATGGGCGC AGGCGGGGCT GGCGATCCCG
       T  H  S  T  H  A  T  A  W  A  Q  A  G  L  A  I  P
      >..................UlaF..........................>

1850  GCGTTAGGCA CCACGCACGC CGACTACTTC TTTGGCGACA TTCCGTGTAC
       A  L  G  T  T  H  A  D  Y  F  F  G  D  I  P  C
      >..................UlaF..........................>

1900  GCGCGGGTTA AGCGAAGAAG AGGTGCAGGG CGAGTATGAA CTGAACACCG
       T  R  G  L  S  E  E  E  V  Q  G  E  Y  E  L  N  T
      >..................UlaF..........................>

1950  GCAAAGTGAT TATCGAAACG CTGGGCAACG CCGAGCCGCT GCATACGCCG
       G  K  V  I  I  E  T  L  G  N  A  E  P  L  H  T  P
      >..................UlaF..........................>

2000  GGAATTGTGG TGTATCAGCA CGGGCCGTTC GCCTGGGGGA AAGATGCTCA
       G  I  V  V  Y  Q  H  G  P  F  A  W  G  K  D  A
      >..................UlaF..........................>

2050  CGATGCGGTG CATAACGCGG TGGTGATGGA AGAAGTGGCG AAAATGGCGT
       H  D  A  V  H  N  A  V  V  M  E  E  V  A  K  M  A
      >..................UlaF..........................>

2100  GGATTGCCCG CGGCATTAAC CCACAACTCA ATCACATCGA CAGCTTCCTG
       W  I  A  R  G  I  N  P  Q  L  N  H  I  D  S  F  L
      >..................UlaF..........................>

2150  ATGAATAAAC ACTTCATGCG TAAACACGGT CCTAACGCTT ATTACGGGCA
       M  N  K  H  F  M  R  K  H  G  P  N  A  Y  Y  G
      >..................UlaF..........................>

2200  GAAGTAGAAC ACGCGCTGCG GAAATTTCCT TCCTCGGGAG ATAACTGGTC
       Q  K  -
      >....>> UlaF

2250  TAATTCCGCA GCCGTTTTTC AAAAAAAAGC CCCCTGCGAA GGGGGCAAAG

SELECTION SYSTEM CONTAINING NON-ANTIBIOTIC RESISTANCE SELECTION MARKER

This application is a U.S. National Stage of International Application No. PCT/FI2004/000540, filed Sep. 15, 2004, and published on Mar. 24, 2005, as WO 2005/026364. This application claims priority to Finnish Patent Application No. FI 20031319, filed Sep. 15, 2003, hereby incorporated by reference for all purposes.

FIELD OF THE INVENTION

The present invention relates to a novel selection system, which is based on the use of an araD gene, a mutated form of an araD gene, a complementary sequence thereof, or a catalytically active fragment thereof as a selection marker and to the use of a bacterial strain deficient of the araD gene. The present invention further relates to novel vectors containing an araD gene, a mutated form of an araD gene, a complementary sequence thereof, or a catalytically active fragment thereof and to novel bacterial strains deficient of an araD gene. The present invention additionally relates to a method of selecting the cells transformed with a plasmid, which contains the gene of interest.

BACKGROUND OF THE INVENTION

An essential requirement for effective genetic engineering of bacteria and other cells propagated in cell cultures is the capacity to select the cells with a specific genotypic alteration. The most common selection strategy in recombinant DNA technology is to include a selection marker in the cloning vector or plasmid. A selection marker can be a cloned gene or a DNA sequence, which allows the separation of the host cells containing the selection marker from those not containing it. The selection marker together with a suitable selection medium maintains the cloning vector in the cells. Otherwise, since the replication of plasmids is an energetic burden for the bacterial host, in a growing culture the bacteria, which have lost the plasmid, would have a growth advantage over the cells with the plasmid.

For most purposes, an antibiotic resistance gene is a commonly used selection marker. However, for the production of recombinant therapeutics, where the goal is to generate a product, such as a DNA vaccine, in high yield for administration in patients, the use of antibiotic resistance genes presents problems: the spread of antibiotic resistant pathogens is a serious worldwide problem [Levy, S. B., J. Antimicrob. Chemother. 49 (2002) 25-30]. Therefore the antibiotic resistance genes cannot have extensive use in the pharmaceutical industry, and for instance, according to the regulations of the U.S. Food and Drug Administration, no antibiotic resistance genes are allowed in experimental DNA vaccines entering the third phase.

Alternatively, antibiotic-free selection systems have been suggested. Such antibiotic-free selection systems include bacterial toxin-antitoxin systems [Engelberg-Kulka, H. and Glaser, G., Annu Rev Microbiol 53 (1999) 43-70], genes responsible for resistance against heavy metals, such as tellurium [Silver, S, and Phung, L. T., Annu Rev Microbiol 50 (1996) 753-789], and systems, in which the plasmid encodes a gene complementing a host auxotrophy [Wang, M. D., et al., J. Bacteriol. 169 (1987) 5610-5614].

US Patent Application 2000/0014476 A1 generally discloses, inter alia, the use of a non-antibiotic selection marker, which may be a gene whose product is necessary for the metabolism of the cell under certain culturing conditions, such as a catabolism gene, which makes it possible for the cell to assimilate a certain substance present in the culture medium (specific carbon or nitrogen source) etc. No specific examples of such suitable genes are given. This approach is not necessarily applicable for commercial production, since the deletion an essential component, such as an amino acid or a carbon source, from the growth medium reduces the yield, which is not desirable. Additionally, the manipulation of the growth medium in terms of omitting an essential nutrient may considerably increase the cost of the growth medium, since commercially available nutrient mixtures must be replaced by individual nutrients.

For commercial therapeutic purposes it would be of advantage to use a gene, which is not essential for the growth of the host but whose manipulation still affects the growth in selected circumstances. Additionally, in view of the therapeutic use, it would be of advantage to use a gene, whose deletion leads to accumulation of compounds, which are toxic to the host cell but not toxic to mammalians, including humans. Also it would be of advantage to use smaller genes, which in turn would allow the construction of smaller plasmids for which the energy consumption for replication is smaller and thus the growth rate of bacterial culture and plasmid yield are improved.

SHORT DESCRIPTION OF THE INVENTION

The object of the present invention is to provide a novel antibiotic-free selection system, which avoids the problems of previously disclosed selection systems for use in the production of recombinant therapeutic products.

Another object of the invention is to provide a novel antibiotic-free selection system, which can be safely used in the production of recombinant therapeutic products in terms of the environment and the patient safety.

A further object of the invention is to provide a novel antibiotic-free selection system, which can be cost-effectively used in the production of recombinant therapeutic products using standard growth mediums.

A still further object of the invention is to provide a novel antibiotic-free selection system, which provides an increased growth rate and improved yield.

Yet another object of the present invention is to provide a novel vector containing a selection marker, which is non-toxic to the environment and to humans and which is capable of a long-term maintenance in the host. Yet another object of the present invention is to provide a novel host cell containing a gene defect, which is not hazardous to the environment.

Still another object of the present invention is to provide a method for selection of cells carrying a gene of interest for the production of recombinant therapeutic products.

It was surprisingly found that the objects of the present invention are met by the use of the araD gene, a mutated form of an araD gene, a complementary sequence thereof, or a catalytically active fragment thereof as a selection marker and the use of a specific bacterial host deficient of the araD gene.

Accordingly, the present invention provides a novel selection system comprising a bacterial cell deficient of an araD gene into which a vector carrying an araD gene, a complementary sequence thereof, or a catalytically active fragment thereof has been added as a selection marker. One embodiment of the present invention relates to a selection system wherein the araD gene is the araD gene or the L-ribulose-5-phosphate 4-epimerase (EC 5.1.3.4.). Another embodiment of the present invention relates to a selection system wherein the araD gene is mutated.

The present invention further provides novel vectors, which contain an araD gene, a mutated form of an araD gene, a complementary sequence thereof, or a catalytically active fragment thereof as a selection marker.

The present invention further provides novel bacterial strains, which are deficient of the araD gene.

The present invention further provides a method of selecting the cells transformed with a plasmid, which contains 1) the araD gene, a mutated form of an araD gene, a complementary sequence thereof, or a catalytically active fragment thereof as a selection marker and 2) the gene of interest, the method comprising inserting said plasmid into the araD deficient host cell and growing the cells in a growth medium containing arabinose.

DRAWINGS

FIG. 1 shows the use of arabinose as a carbon source by the E. coli cells (Lin, 1987).

FIG. 2 shows the map of S6wtd1EGFP. The coding sequences for the d1EGFP, E2 and kanamycin resistance marker aminoglycoside-3'-O-phosphotransferase (kana) are indicated by arrows. Additional features are indicated by solid boxes: 10E2BS—ten BPV E2 binding sites with high affinity; CMV-tk—human cytomegalovirus immediately early promoter and HSV Th gene leader sequence; intron—rabbit beta-globin gene intron with optimized SD and SA sites; tkpa—HSV Tk gene polyadenylation signal; RSV LTR—Rous sarcoma virus long terminal repeat; bgh pA—bovine growth hormone gene polyadenylation signal; pUCori—bacterial origin of replication derived from the pUC18 plasmid.

FIG. 3 shows the map of S6wtd1EGFPkana/araD1. The coding sequences for the d1EGFP, E2, kanamycin resistance marker aminoglycoside-3'-O-phosphotransferase (kana) and L-ribulose-5-phosphate 4-epimerase (araD) are indicated by arrows. Additional features are indicated by solid boxes: 10E2BS—ten BPV E2 binding sites with high affinity; CMV-tk—human cytomegalovirus immediately early promoter and HSV Th gene leader sequence; intron—rabbit beta-globin gene intron with optimized SD and SA sites; tkpa—HSV Tk gene polyadenylation signal; RSV LTR—Rous sarcoma virus long terminal repeat; bgh pA—bovine growth hormone gene polyadenylation signal; pUCori—bacterial origin of replication derived from the pUC18 plasmid.

FIG. 4 shows the map of S6wtd1EGFPkana/araD2. The coding sequences for the d1EGFP, E2, kanamycin resistance marker aminoglycoside-3'-O-phosphotransferase (kana) and L-ribulose-5-phosphate 4-epimerase (araD) are indicated by arrows. Additional features are indicated by solid boxes: 10E2BS—ten BPV E2 binding sites with high affinity; CMV-tk—human cytomegalovirus immediately early promoter and HSV Th gene leader sequence; intron—rabbit beta-globin gene intron with optimized SD and SA sites; tkpa—HSV Tk gene polyadenylation signal; RSV LTR—Rous sarcoma virus long terminal repeat; bgh pA—bovine growth hormone gene polyadenylation signal; pUCori—bacterial origin of replication derived from the pUC18 plasmid.

FIG. 5 shows the map of S6wtd1EGFP/araD1. The coding sequences for the d1EGFP, E2 and L-ribulose-5-phosphate 4-epimerase (araD) are indicated by arrows. Additional features are indicated by solid boxes: 10E2BS—ten BPV E2 binding sites with high affinity; CMV-tk—human cytomegalovirus immediately early promoter and HSV Th gene leader sequence; intron—rabbit beta-globin gene intron with optimized SD and SA sites; tkpa—HSV Tk gene polyadenylation signal; RSV LTR—Rous sarcoma virus long terminal repeat; bgh pA—bovine growth hormone gene polyadenylation signal; pUCori—bacterial origin of replication derived from the pUC18 plasmid.

FIG. 6 shows the map of S6wtd1EGFP/araD2. The coding sequences for the d1EGFP, E2 and L-ribulose-5-phosphate 4-epimerase (araD) are indicated by arrows. Additional features are indicated by solid boxes: 10E2BS—ten BPV E2 binding sites with high affinity; CMV-tk—human cytomegalovirus immediately early promoter and HSV Th gene leader sequence; intron—rabbit beta-globin gene intron with optimized SD and SA sites; tkpa—HSV Tk gene polyadenylation signal; RSV LTR—Rous sarcoma virus long terminal repeat; bgh pA—bovine growth hormone gene polyadenylation signal; pUCori—bacterial origin of replication derived from the pUC18 plasmid.

The abbreviations are as follows: sPump=feeding speed; pO2=the oxygen concentration; Temp=growth temperature; mys=desired growth rate; OD=optical density at 600 nm.

Figure 12:
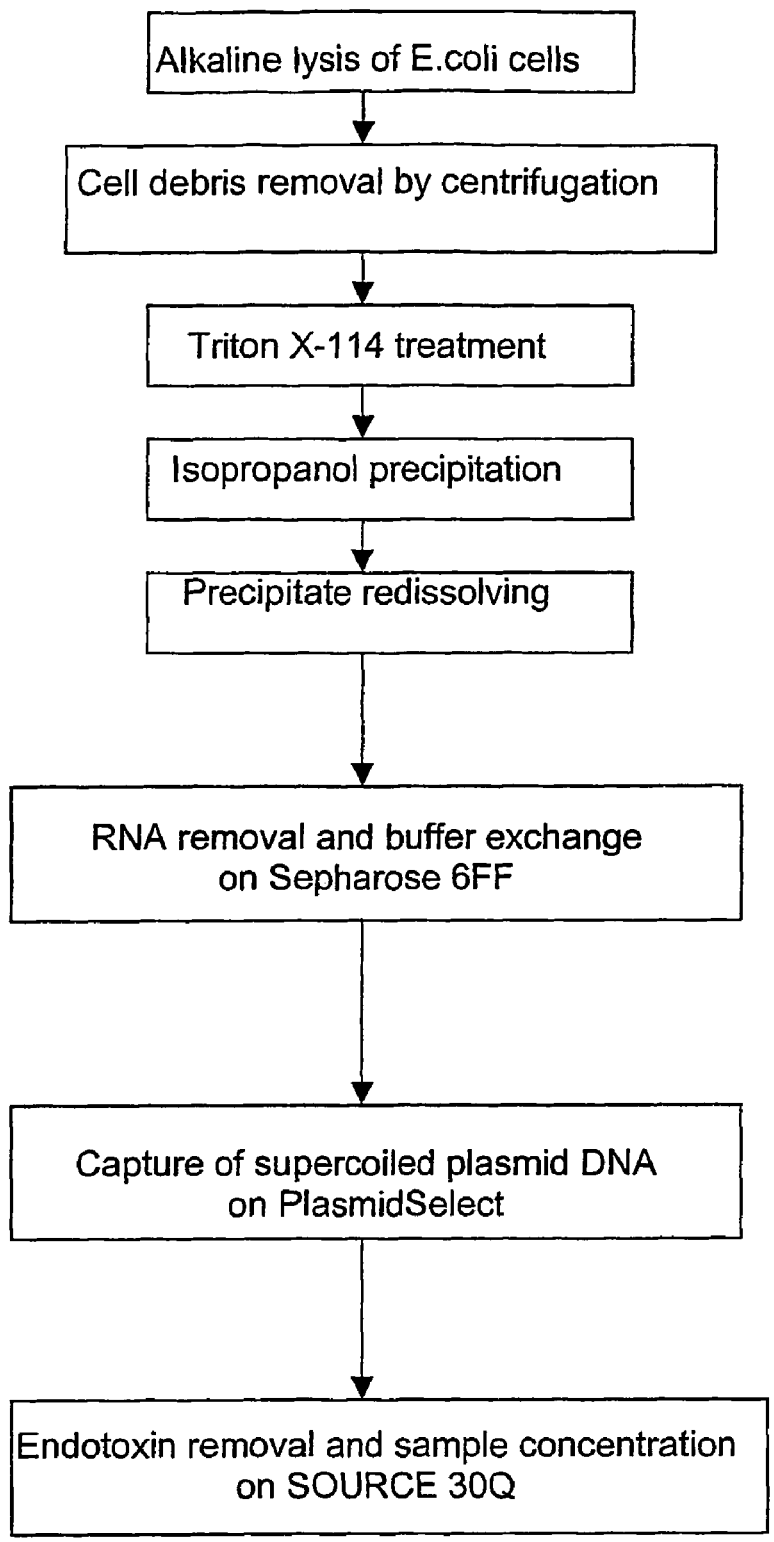

FIG. 12 shows the scheme of lysis and purification of AG1ΔaraD S6wtd1EGFP/araD2.

FIG. 13 shows the araD locus sequence of clone #13. The polynucleotide sequence is SEQ ID NO: 19. The polypeptide sequence is SEQ ID NO: 34.

Figure 14:
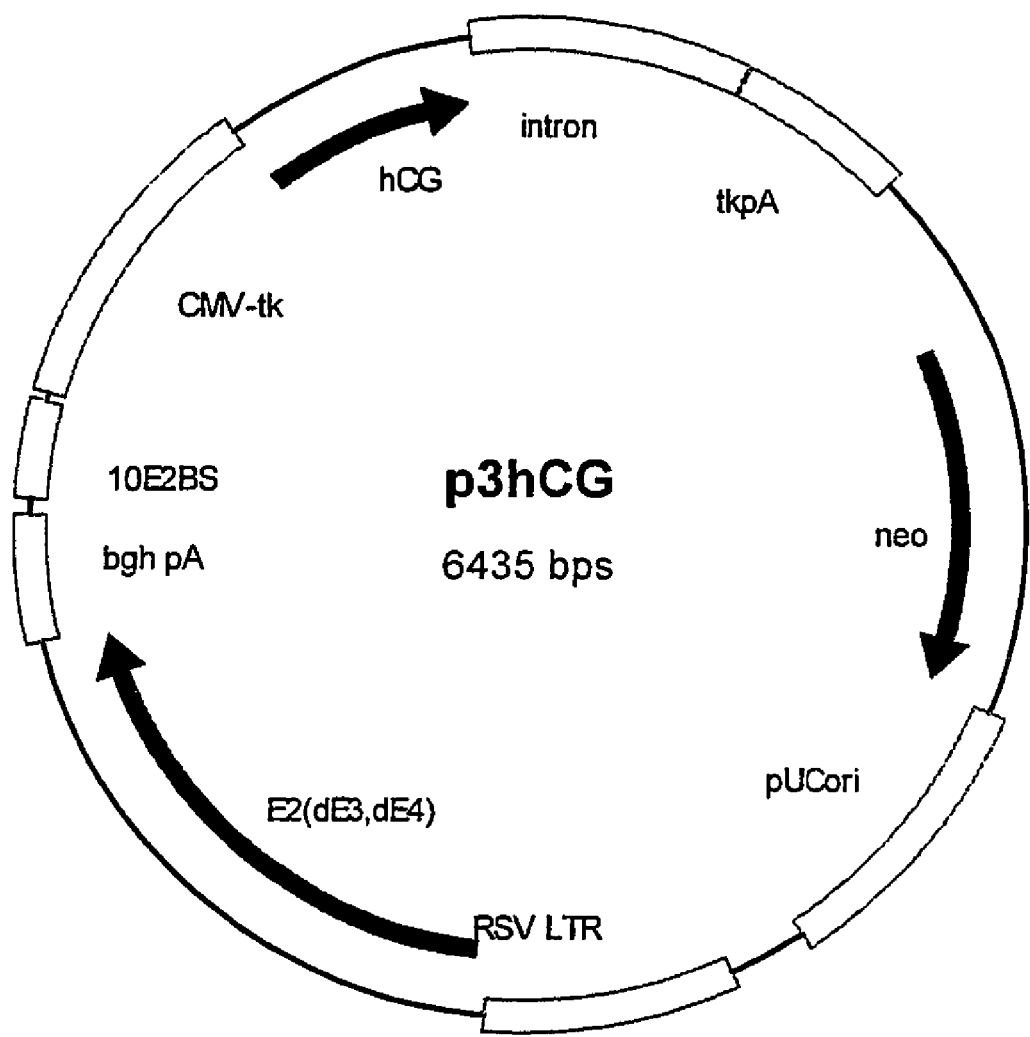

FIG. 14 shows the map of plasmid p3hCG.

Figure 15:
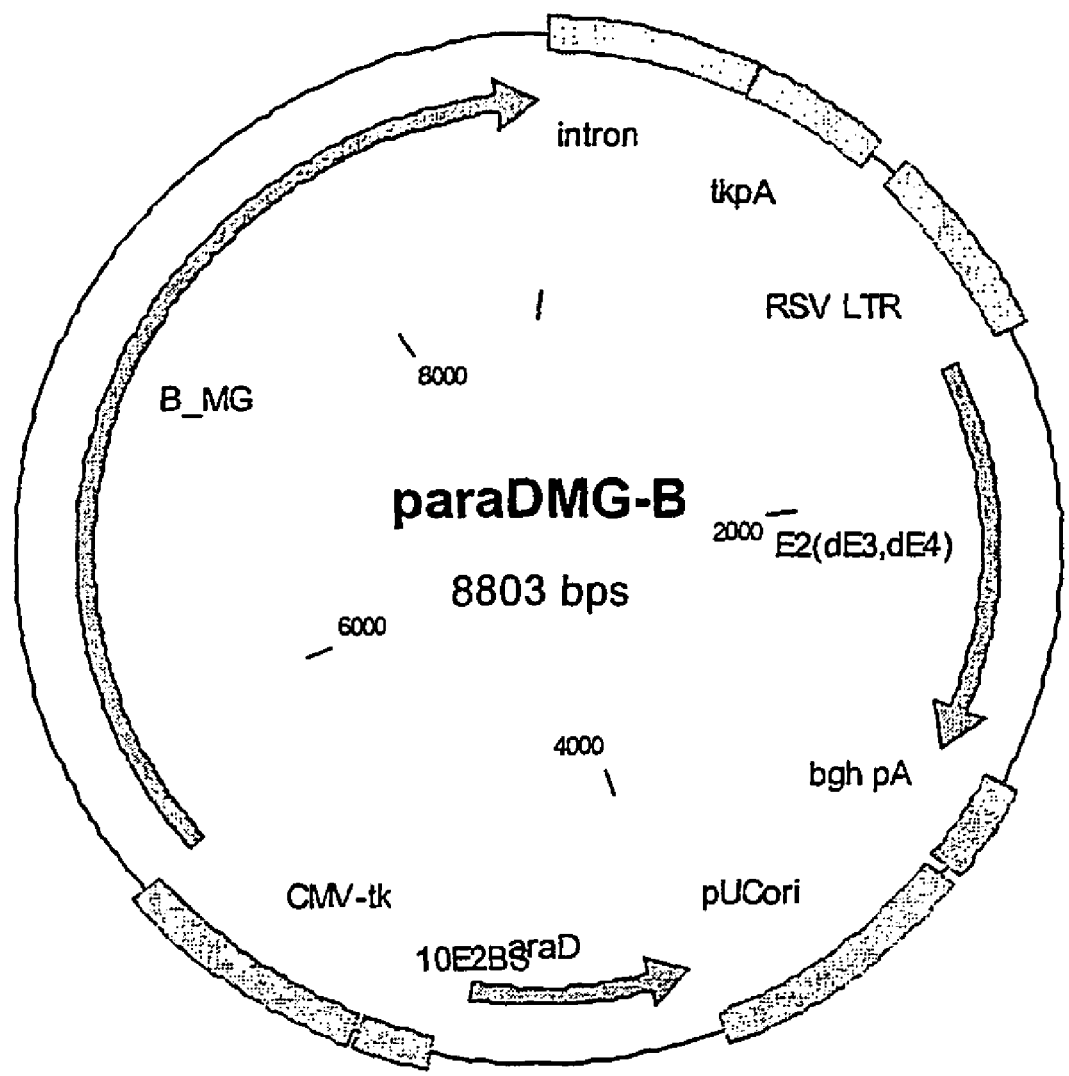

FIG. 15 shows the map of plasmid paraDMgB.

Figure 16:
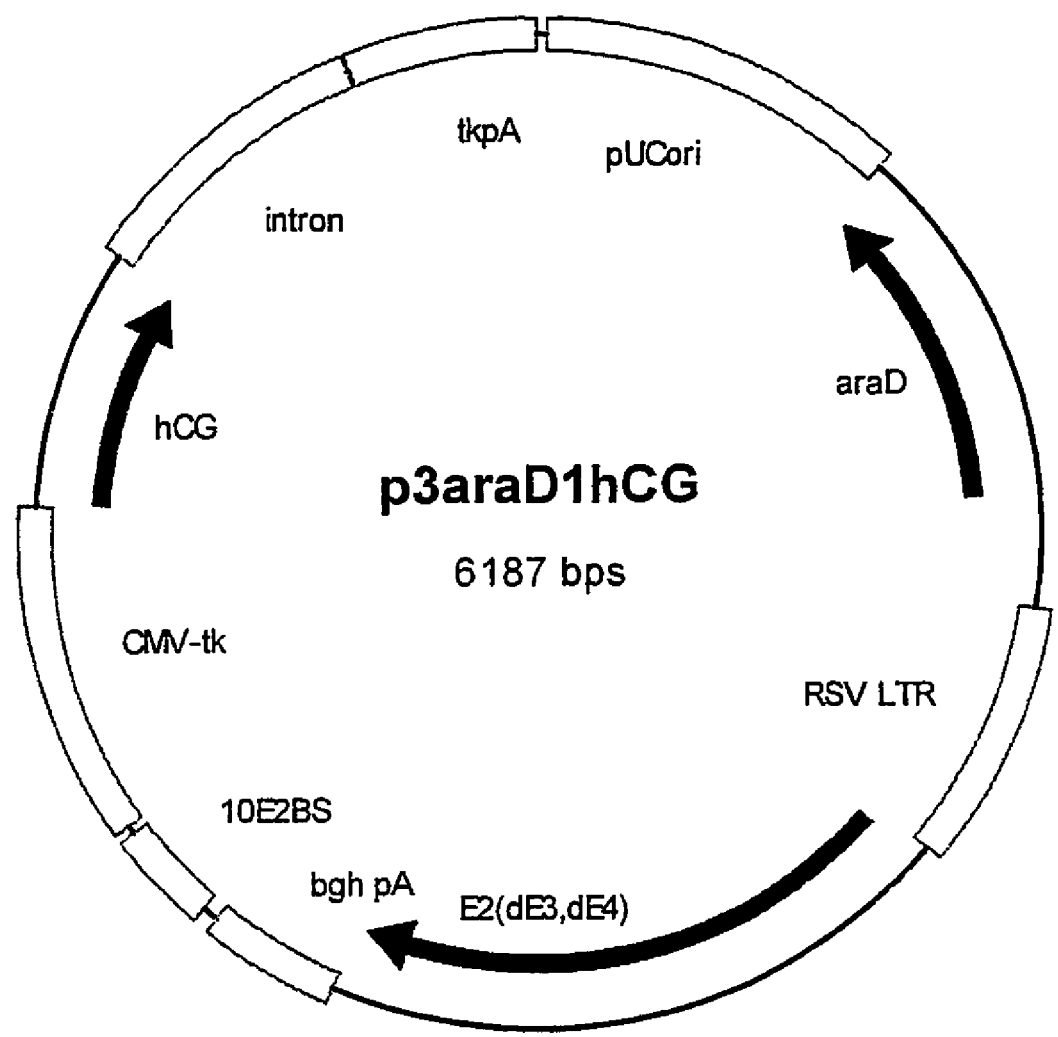

FIG. 16 shows the map of plasmid p3araD1hCG.

Figure 17:
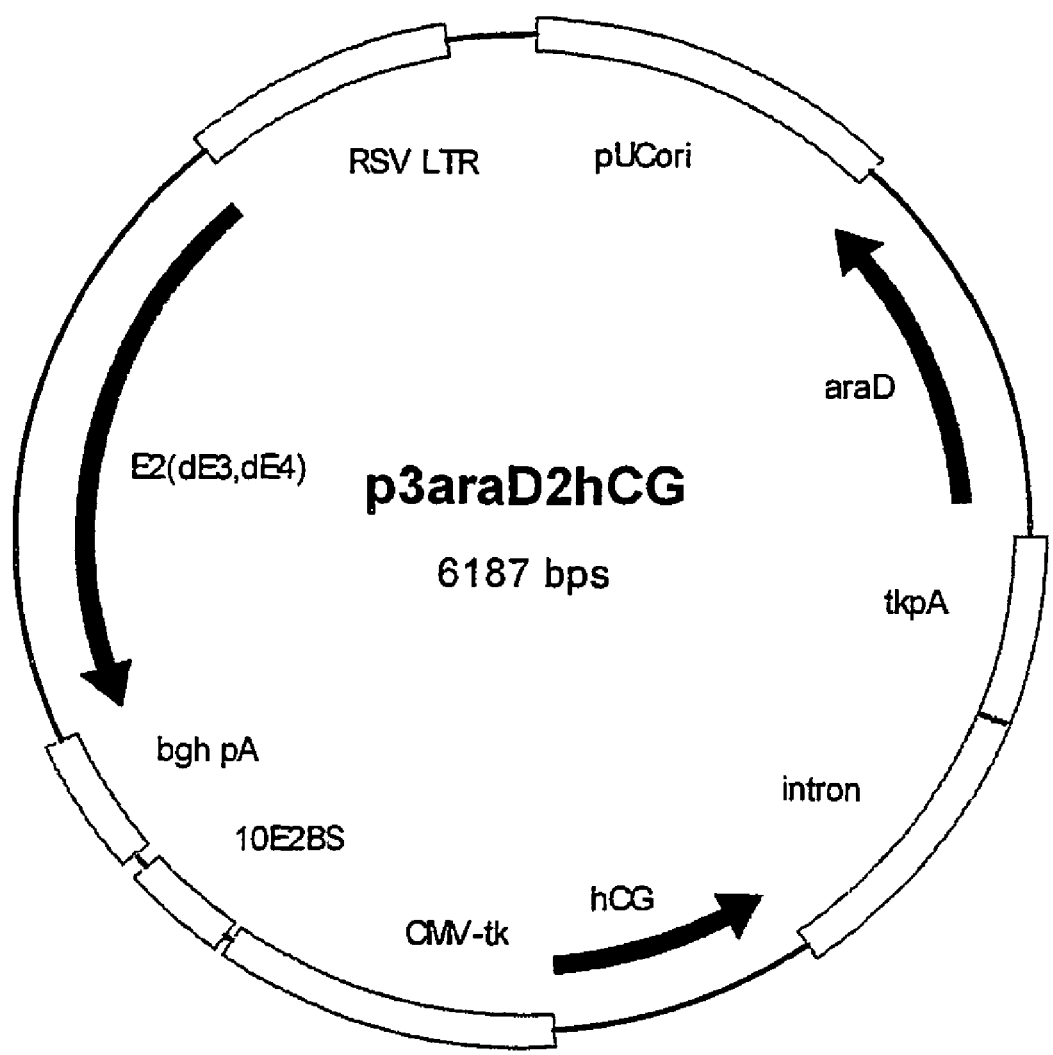

FIG. 17 shows the map of plasmid p3araD2hCG.

Figure 18:
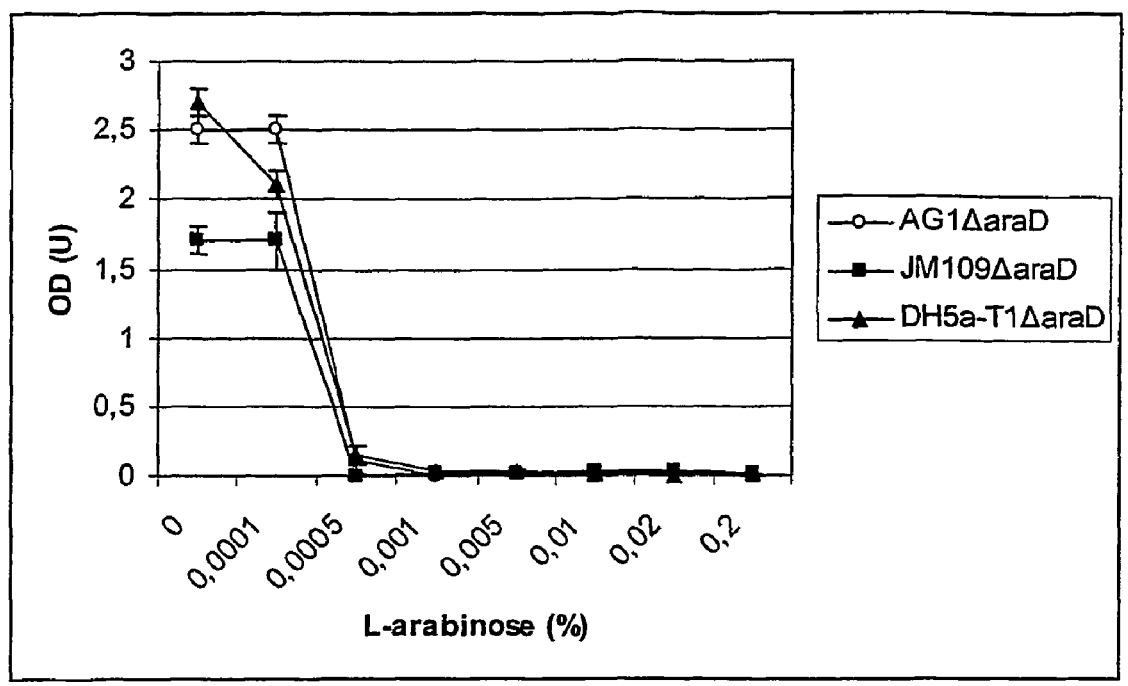

FIG. 18 shows the results of the analysis of L-arabinose sensitivity of E. coli strains with disrupted araD.

Figure 19:
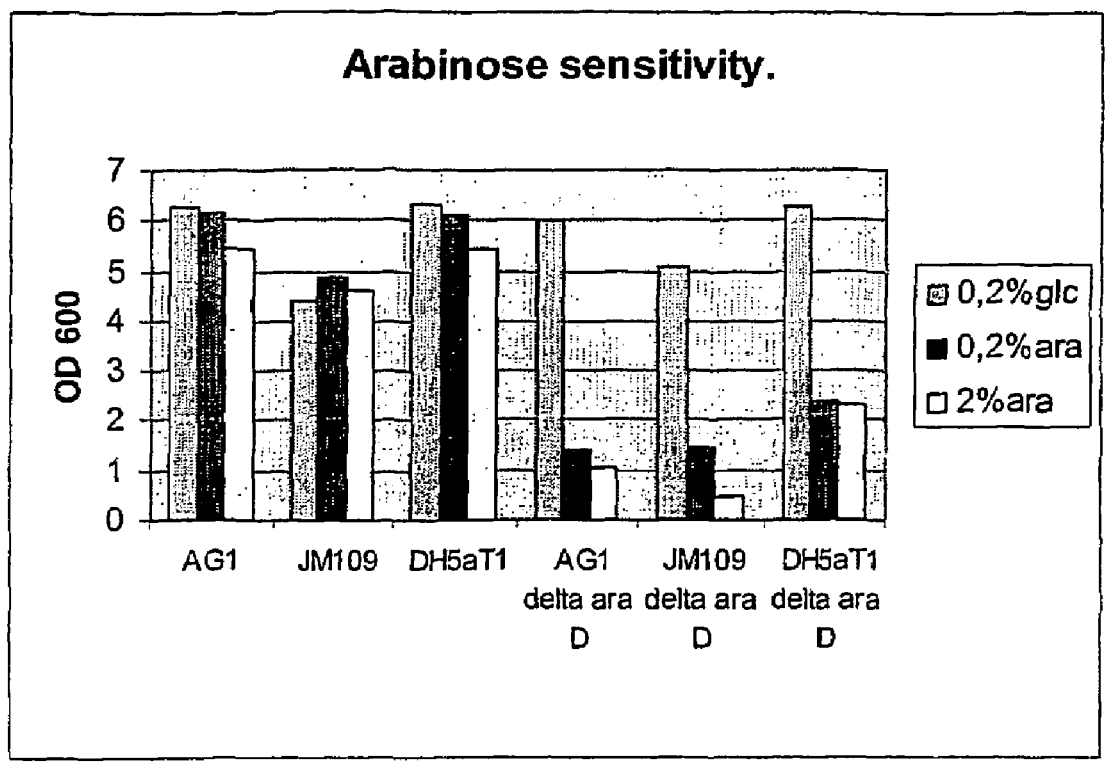

FIG. 19 shows the results of the analysis of the L-arabinose sensitivity in M9 and yeast extract medium with different glucose and arabinose concentrations.

Figure 20:
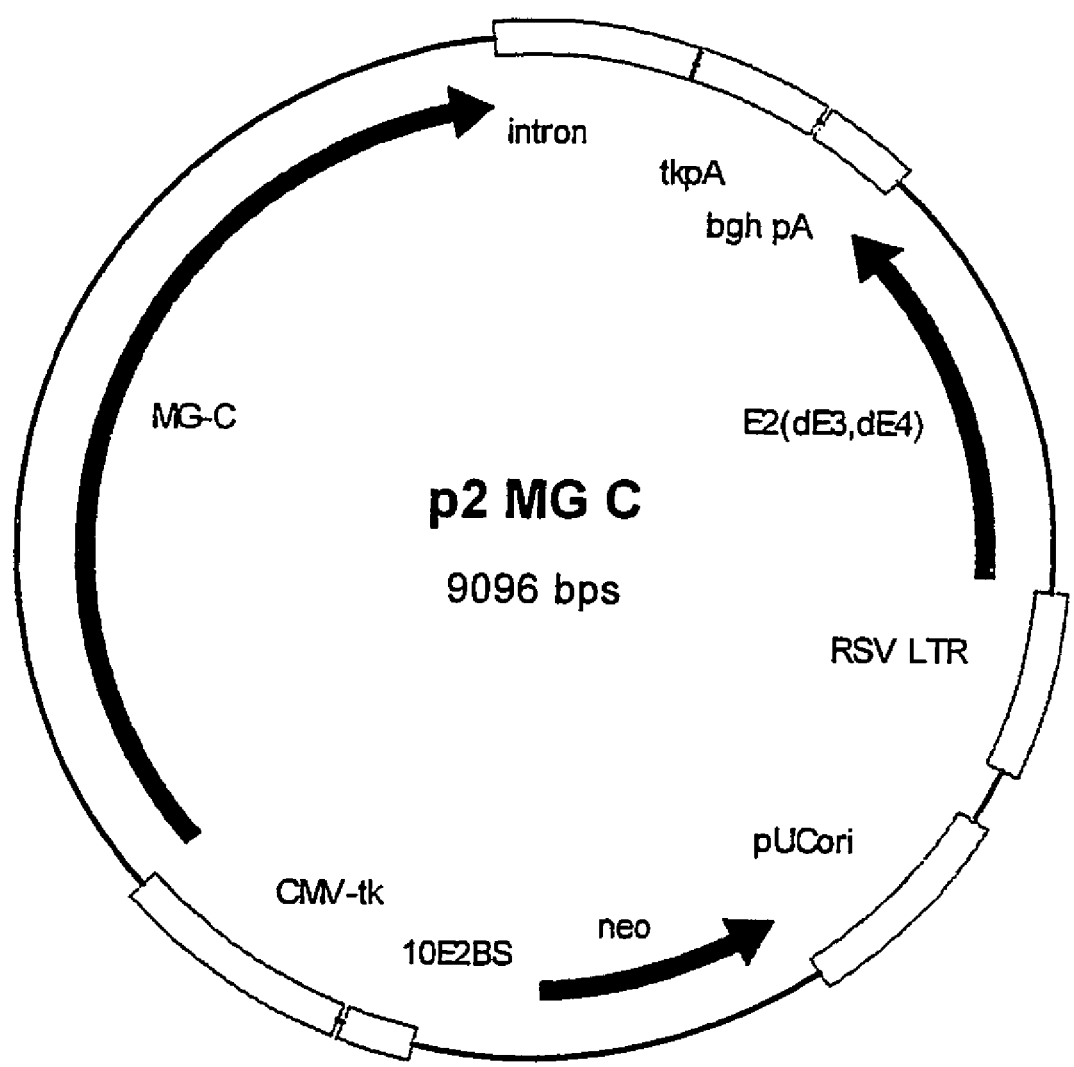

FIG. 20 shows the map of plasmid p2 MG C #11.

Figure 21:
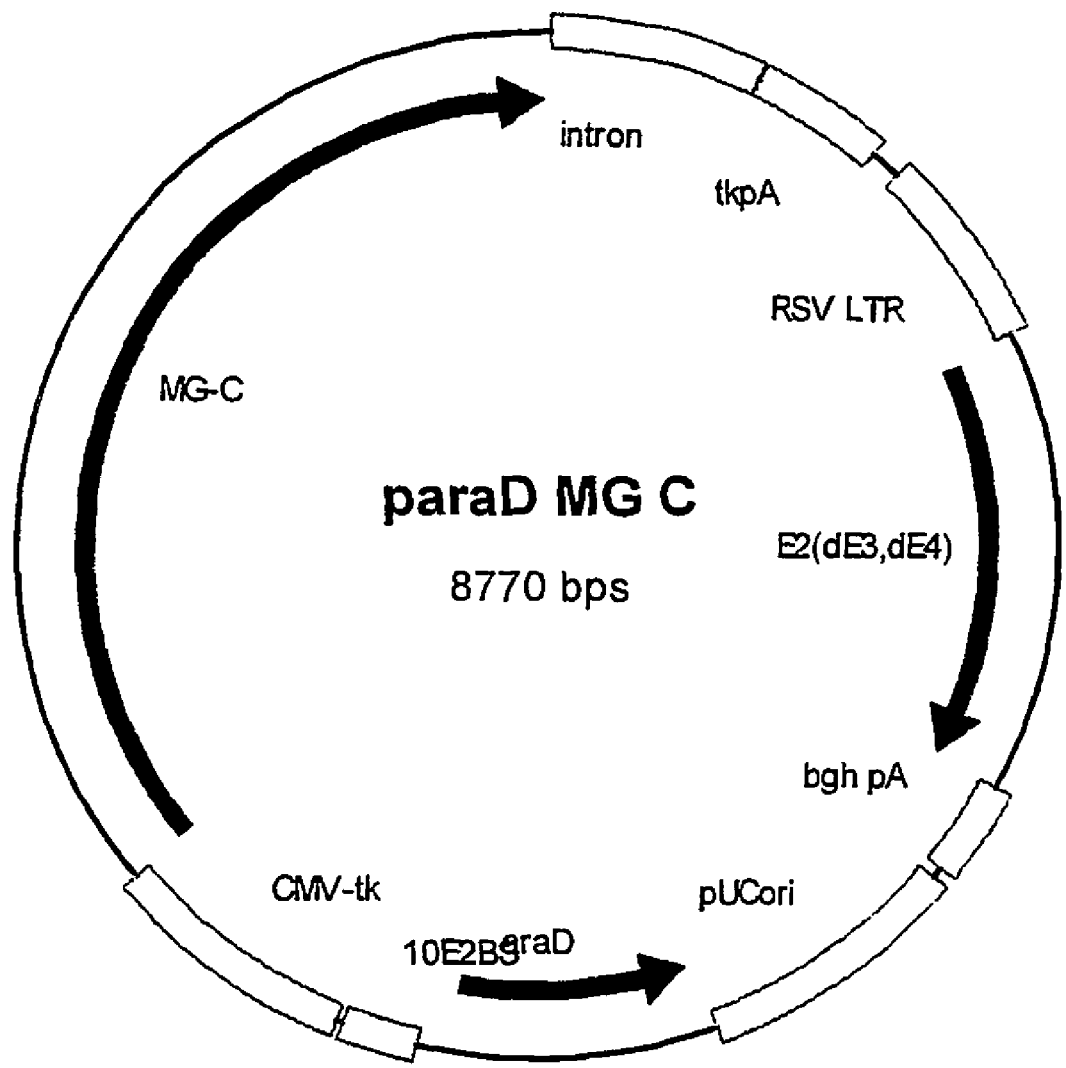

FIG. 21 shows the map of plasmid paraD MG C #145.

Figure 22:
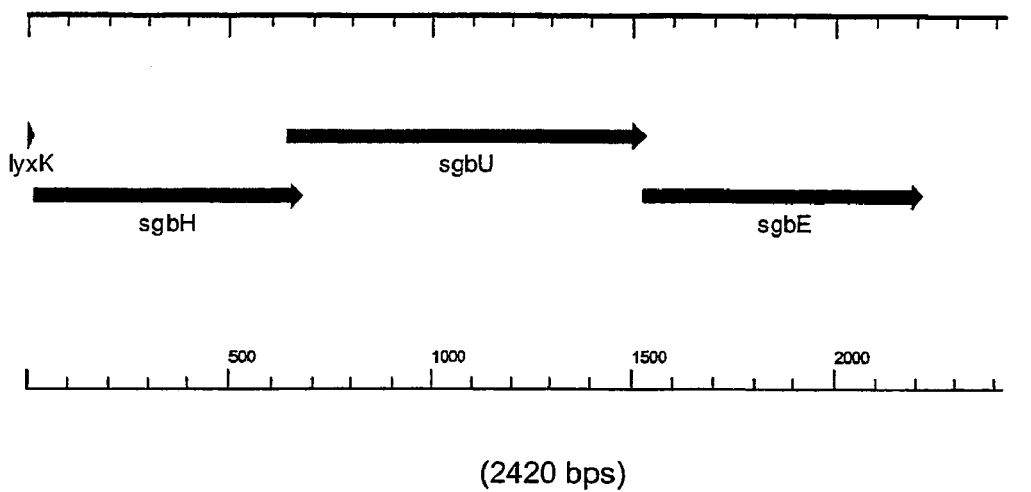

FIG. 22 shows the E. coli genomic fragment containing the sgbE gene. The polynucleotide sequence is SEQ ID NO: 30. The polypeptide sequence is SEQ ID NO: 31.

Figure 23:
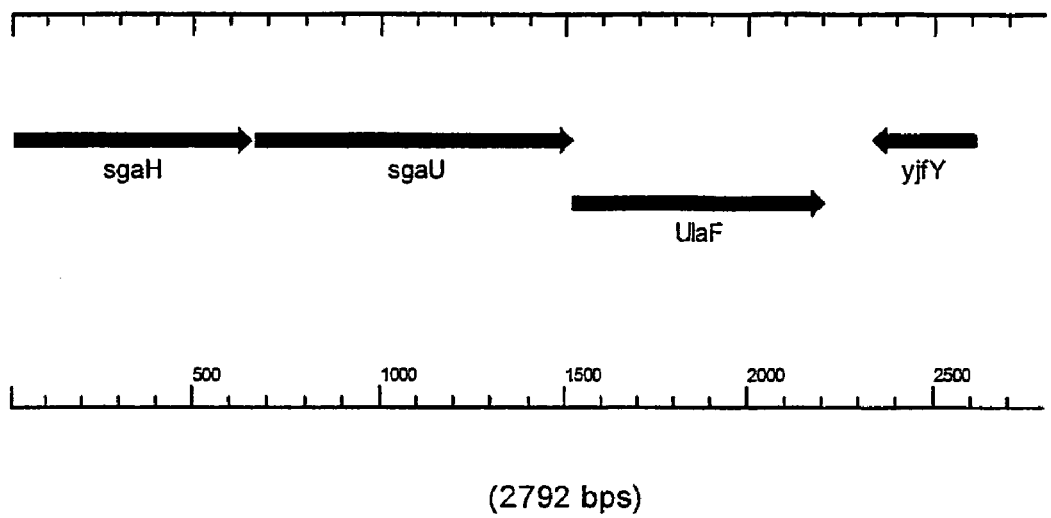

FIG. 23 shows the E. coli genomic fragment containing ulaF gene. The polynucleotide sequence is SEQ ID NO: 32. The polypeptide sequence is SEQ ID NO: 33.

DETAILED DESCRIPTION OF THE INVENTION

The present invention is based on an effort to find an alternative, antibiotic-free selection system, which could be used in the production of recombinant therapeutic products to be administered in vivo, especially in the production of DNA vaccines. Surprisingly it was found that the araD gene involved in the pentose phosphate pathway of both prokaryotic and eukaryotic organisms, such as mammalians including humans, can be successfully used as a selection marker in an auxotrophic host cell for the plasmid. The use of the auxotrophy has the advantage of not involving a use or generation of toxic substances that could later contaminate the plasmid preparation.

An efficient selection system has been constructed on the basis of araD/araC genes [Ariza, R. R., et al., Carcinogenesis 14 (1993) 303-305]. However, this selection system has been used in the studies on the mechanisms of mutagenesis but not used before as a selection marker for plasmid maintenance. Ariza et al. used a strain where the araC gene contains a termination codon and the araD gene is inactivated. A product of the supF gene, which codes for a suppressor tRNA, was introduced on the plasmid. In the presence of active suppressor tRNA, enzymatically active product from araC was produced causing cell growth arrest (because araD was inactive). This system allows to study the suppression of mutations by supF tRNA: in case supF is inactivated by mutation, the cells can grow on arabinose. Therefore, this selection system is based on araC gene and not on araD gene. araD was not introduced into a plasmid, nor was the system designed or characterized for plasmid production purposes.

Figure 1:
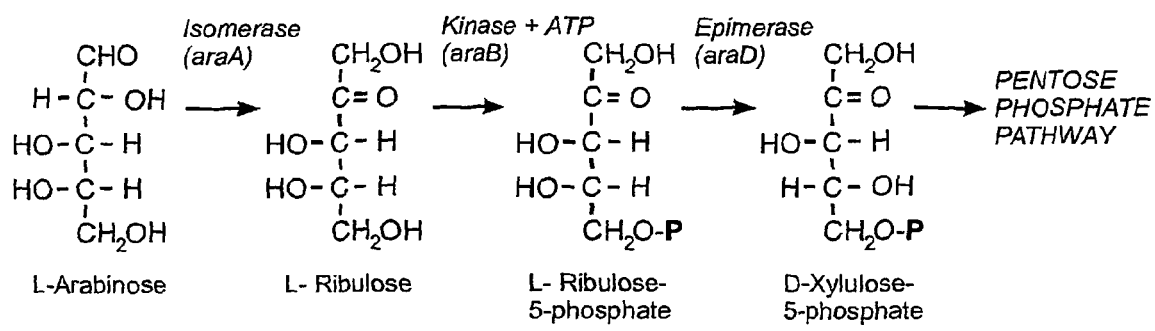

The araD gene codes for an enzyme which is responsible for epimerization of ribulose-5-phosphate to xylulose-5-phosphate (FIG. 1) and therefore allows the use arabinose in the pentose phosphate pathway [Engelsberg, E., et al., J. Bacteriol. 84: (1962) 137-146]. If araD is inactivated, ribulose-5-phosphate accumulates in the bacterial cell leading to growth arrest.

If the chromosomal copy of araD is inactivated in the host cell and an intact copy of the araD gene, a mutated form of the araD gene, a complementary sequence thereof, or a catalytically active fragment thereof is inserted into the plasmid, the growth advantage of the plasmid-containing cells in medium containing L-arabinose is achieved as a result from two effects. First, the plasmid-containing cells can use arabinose as a carbon source, and second, the toxic ribulose-5-phosphate does not accumulate. This allows the use of rich growth media supplemented with arabinose. In rich media the *E. coli* cells grow fast and the plasmid yield is high. Inexpensive standard components of the bacterial growth media, such as yeast extract, can be used as an amino acid source. The traces of ribulose-5-phosphate that theoretically could contaminate the plasmid preparation are not a problem, when the preparation is administered in vivo, as ribulose-5-phosphate can be efficiently metabolized by human cells and is not toxic.

The use of mutated form of the araD gene offers particular advantages. Selection systems of the invention comprising a bacterial cell deficient of an araD gene into which a vector carrying a mutated form of the araD gene as a selection marker produce an optimal concentration of the araD gene product L-ribulose-5-phosphate 4-epimerase to afford rapid uninhibited growth of the bacteria. Similar advantaged are obtained by the use selection systems containing a vector carrying an intact araD gene but comprising deletions or mutations elsewhere in the araD gene locus.

The selection system of the invention comprises 1) a vector carrying an araD gene, a mutated form of the araD gene, a complementary sequence thereof, or a catalytically active fragment thereof as a selection marker and 2) a specific bacterial strain deficient of the araD gene into which the vector has been added. When the specific host deficient of the araD gene is cultured in the presence of arabinose, the only surviving cells are those containing the vector, which contains an araD gene, a mutated form of the araD gene, a complementary sequence thereof, or a catalytically active fragment thereof.

In the selection system of the invention any expression vector commonly used in the production of therapeutic products can be employed, whereby the araD gene, a mutated form of the araD gene, a complementary sequence thereof, or a catalytically active fragment thereof is inserted into the vector using methods generally known in the art. In the present context, the araD gene preferably comprises the sequence identified by SEQ ID NO. 1, by SEQ ID NO. 19, or a sequence hybridizable thereto. However, any applicable araD genes are also contemplated. In the present context, the term "a catalytically active fragment of the araD gene" is any gene fragment coding a polypeptide or a protein capable of epimerization of L-ribulose-5-phosphate to D-xylulose-5-phosphate. In a specific embodiment of the invention the araD gene, a complementary sequence thereof, or a catalytically active fragment thereof is inserted in the vector capable of a long-term maintenance and thereby capable of providing a stable expression of the desired antigen(s).

In another specific embodiment of the invention a mutated form of an araD gene, a complementary sequence thereof, or a catalytically active fragment thereof is inserted in the vector capable of a long-term maintenance and thereby capable of providing a stable expression of the desired antigen(s).

In a specifically preferred embodiment of the invention the vector used is an expression vector comprising:

(a) a DNA sequence encoding a nuclear-anchoring protein operatively linked to a heterologous promoter, said nuclear-anchoring protein comprising (i) a DNA binding domain which binds to a specific DNA sequence, and (ii) a functional domain that binds to a nuclear component, or a functional equivalent thereof; and (b) a multimerized DNA sequence forming a binding site for the nuclear anchoring protein, wherein said vector lacks a papilloma virus origin of replication, and (c) an araD gene, a mutated form of an araD gene, a complementary sequence thereof, or a catalytically active fragment thereof.

Such vectors have been described in detail in the international patent application WO02/090558, which is incorporated herein by reference.

Most preferably the vector used in the selection method of the present invention is an expression vector comprising:

(a) the E2 protein of Bovine Papilloma Virus type 1 (BPV), and (b) multiple binding sites of the BPV E2 protein incorporated into the vector as a cluster, where the sites can be as head-to-tail structures or can be included into the vector by spaced positioning, wherein said vector lacks a papilloma virus origin of replication, and (c) the araD gene, a complementary sequence thereof, or a catalytically active fragment thereof.

In the selection system of the invention in principle any known host deficient of the araD gene and suitable for use in the production of therapeutic products could be employed. In the present connection the term "deficient" denotes a host, in which the araD gene is either totally deleted or inactivated by any known method.

In a preferred embodiment of the invention an *Escherichia coli* strain, preferably commercially available *E. coli* strains DH5alpha-T1, AG1 or JM109, from which the araD gene has been deleted with generally known methods, such as those described below in the Examples, is used. In another preferred embodiment of the invention an *E. coli* strain, preferably *E. coli* strain DH5alpha-T1, AG1 or JM109, into which combined deletions have been made for depletion of other genes encoding proteins with L-ribulose-5-phosphate 4-epimerase activity. Alternatively, commercially available *E. coli* strains, preferably *E. coli* strains DH5alpha-T1, AG1 or JM109, in which the araD gene and/or other genes encoding proteins with L-ribulose-5-phosphate 4-epimerase activity have been inactivated by any known method can be employed. In the method for selection of cells carrying a gene of interest for the production of recombinant therapeutic products, the gene of interest is inserted into host cells deficient of an araD and/or other genes encoding proteins with L-ribulose-5-phosphate 4-epimerase activity using method well known in the art and the cells are cultured in a growth medium containing arabinose under culturing medium and conditions suitable the host in question.

Any growth medium suitable for culturing *E. coli* cells can be used. For commercial production the growth medium will naturally be optimized in terms of the yield. Examples of suitable growth media are commercially available growth media, such as M9 and LB (available from several manufacturers, such as Fermentas, Lithuania). The amount of arabinose added in the growth medium is not critical but naturally arabinose should be present in an amount that is sufficient for the total culturing period. As low amount as 0.1% has been found sufficient for the selection. Typically arabinose is added to the medium in an amount of about 0.1% to about 2.0%, preferably in an amount of about 0.2% to about 1,0%, most preferably 0.2% to about 0.5%. However the effect of L-arabinose is observed at concentrations as low as 0.01% and L-arabinose can be added up to 5% in the growth medium. In a special embodiment, where L-arabinose is used both as a selecting agent and as a limited carbon source, 0.2% of L-arabinose is a suitable amount to be added into the growth medium.

The selection system of the invention is suitable for use in any expression system. It is especially suitable for use in the expression of recombinant therapeutic products, such as DNA vaccines, intended for use in vivo, since the problems associated with the use of antibiotic resistance genes are avoided. Likewise the selection system of the invention is suitable for use in the production of recombinant proteins.

The possible contamination of arabinose in the final product resulting from the preparation process is inconsequential, since arabinose is editable sugar contained in foods naturally and as an additive and thus not toxic to mammalians including humans.

Additionally, the araD gene is smaller in size than the commonly used antibiotic resistance genes against, for instance, ampicillin and tetracyclin and of similar size to kanamycin and chloramphenicol resistance genes. This affords an additional advantage, since it allows the construction of small plasmids for which the energy consumption for replication is smaller than for large plasmids. Thereby both the growth rate of bacterial culture and plasmid yield are increased.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

Cloning of araD Selection Plasmids

Figure 2:
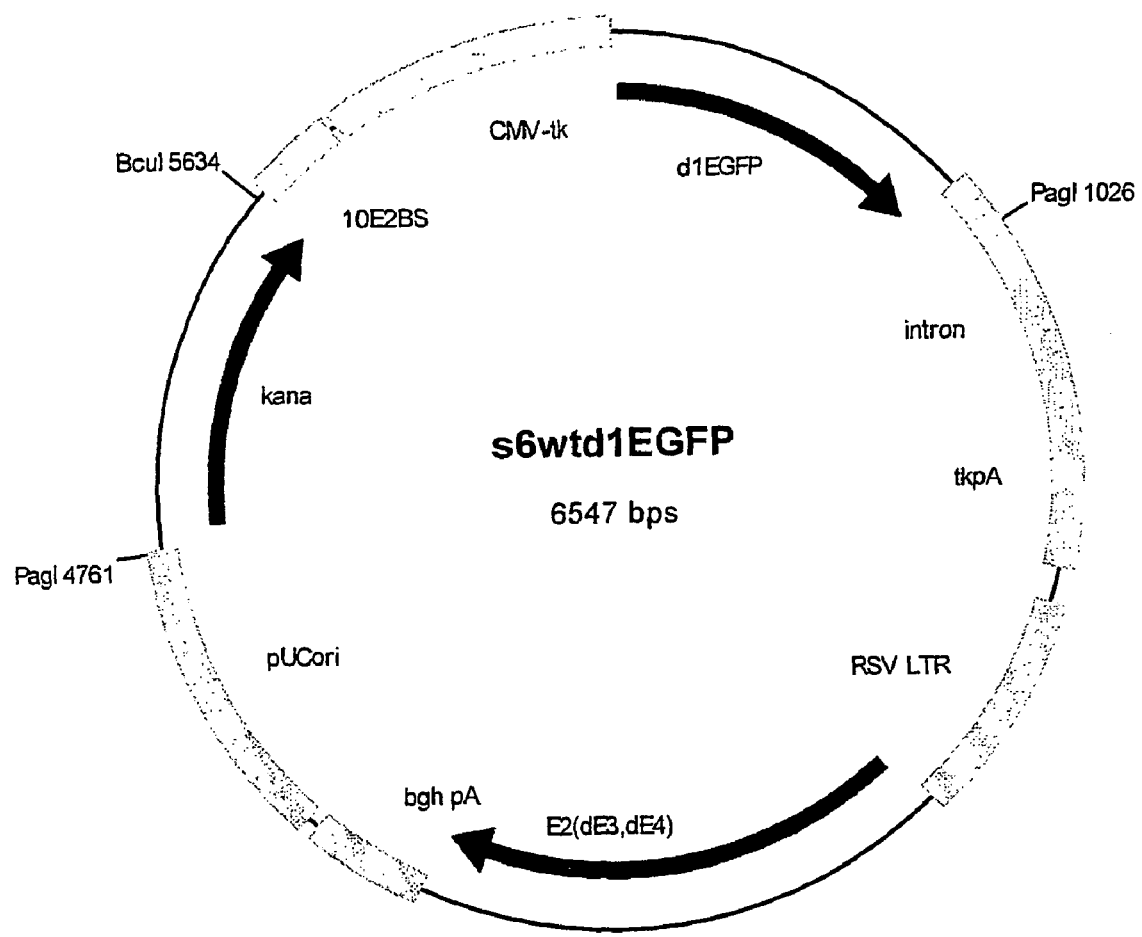

For cloning araD selection constructs plasmid S6wtd1EGFP (FIG. 2) was used. It has pMB1 origin of replication and kanamycin resistance marker as functional elements of plasmid backbone. The kanamycin resistance in this plasmid is conferred by gene that is derived from *E. coli* transposon Tn903.

The araD gene was amplified using polymerase chain reaction (PCR) from *E. coli* DH5α chromosome according to standard procedure. The PCR product was cloned into selected plasmids in two different orientations with the primer pairs s6araDL1+s6araDR1 or s6araDL1+s6araDR1, generating products named araD1 and araD2, respectively:

s6araDL1:
CGCCATGGTTCTCATGTTTGACAGCT-
TATCATCGATAAGCTTTA ATGCGGTAGTTTAGCAC-
GAAGGAGTCAACATG (SEQ ID NO. 2);

s6araDR1:
CGCCATGGACTAGTAAAAAAAAGC-
CCGCTCATTAGGCGGGCT GTCATTACTGCCCG-
TAATATGC (SEQ ID NO. 3);

s6araDL2:
CGCCATGGACTAGTTCTCATGTTTGA-
CAGCTTATCATCGATAAG CTTTAATGCGGTAGTT-
TAGCACGAAGGAGTCAACATG (SEQ ID NO. 4);

s6araDR2:
CGCCATGGAAAAAAAAGCCCGCTCATT-
AGGCGGGCTGTCATTACTGCCCGTAATATGC (SEQ ID NO. 5);

The primers were designed so that P2 promoter from plasmid pBR322 (used for driving the tetracycline resistance gene in pBR322) and termination sequence from trp operon of *E. coli* were added during PCR to the upstream and downstream of araD coding sequence, respectively.

PCR products of 814 and 815 bp were cloned into pUC18 vector linearized with HincII (Fermentas, Lithuania) and correct sequences were verified by sequencing using universal sequencing primers M13F22: GCCAGGGTTTTCCCAGTCACGA (SEQ ID NO. 6) and M13R24: GAGCGGATAACAATTTCACACAGG (SEQ ID NO. 7) and araD specific primers araD F311: CCAACTCACCGGCTGCTCTATC (SEQ ID NO. 8), araD F614: AATGCCGAAGATGCGGTGCATAAC (SEQ ID NO. 9), araD R700: TAACTGCGGCGCTAACTGAC (SEQ ID NO. 10), and araD R421: GGTTGCTGGAATCGACTGAC (SEQ ID NO. 11).

The mutations in amplified sequences were repaired by recombination of different clones.

For cloning araD into S6wtd1EGFP, the vector was linearized by partial digestion with restriction enzyme PagI (position 4761) (Fermentas, Lithuania) and the DNA 5'-termini were dephosphorylated with Calf Intestine Alkaline Phosphatase (CIAP; Fermentas, Lithuania). araD1 and araD2 fragments were cut out from pUC18 with NcoI (Fermentas, Lithuania) and ligated to S6wtd1EGFP/PagI.

Both ligation mixtures were transformed into *E. coli* DH5a competent cells and plated onto dishes containing LB medium containing 50 µg/ml kanamycin and incubated at 37° C. over night. Colonies were first analysed with colony PCR, after which the DNA was isolated and digested with different restriction enzymes.

Figure 3:
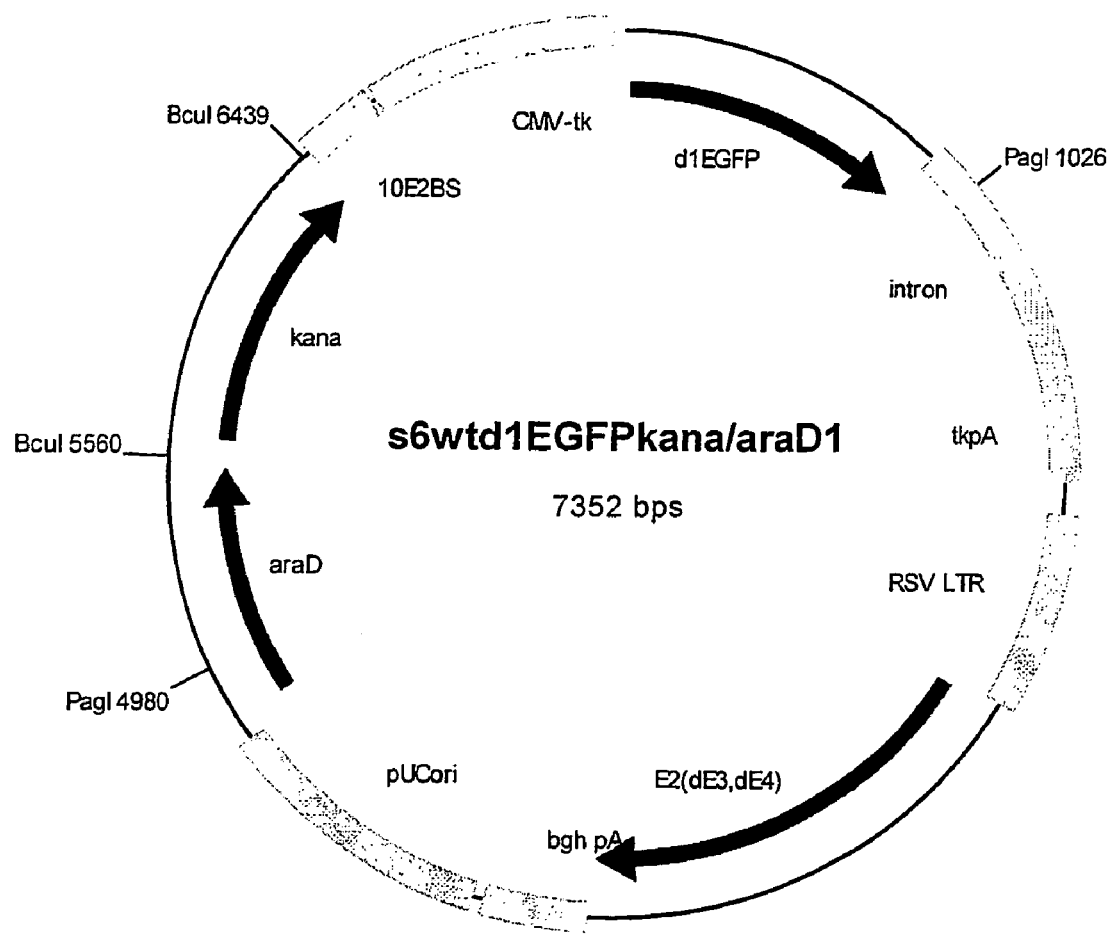
Figure 4:
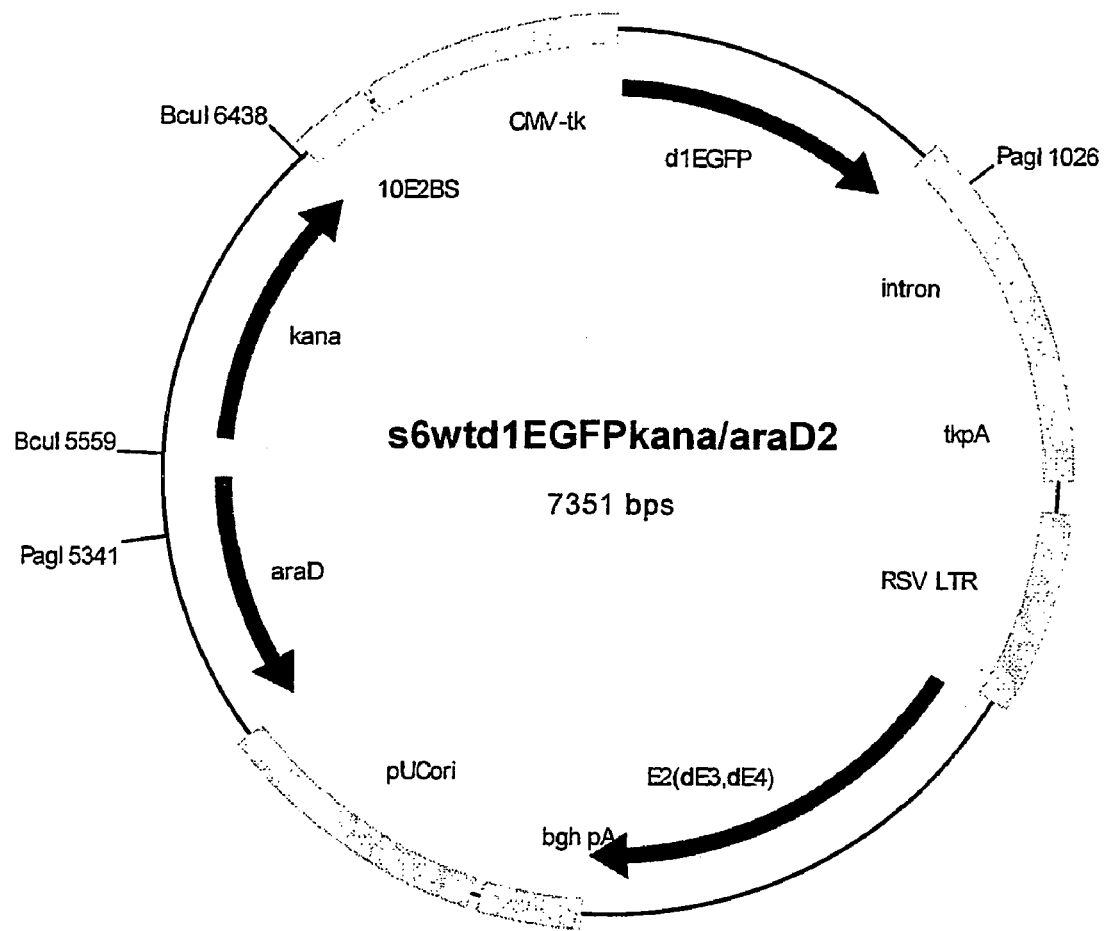

The cloning resulted in plasmids S6wtd1EGFPkana/araD1, S6wtd1EGFPkana/araD2, which are shown in FIGS. 3 and 4.

To remove the kanamycin resistance marker gene from the plasmids, S6wtd1EGFPkana/araD1 and S6wtd1EGFPkana/araD2 were digested with restriction endonuclease Bcul (Fermentas, Lithuania) and a 6473 bp vector fragment was self-ligated.

Figure 5:
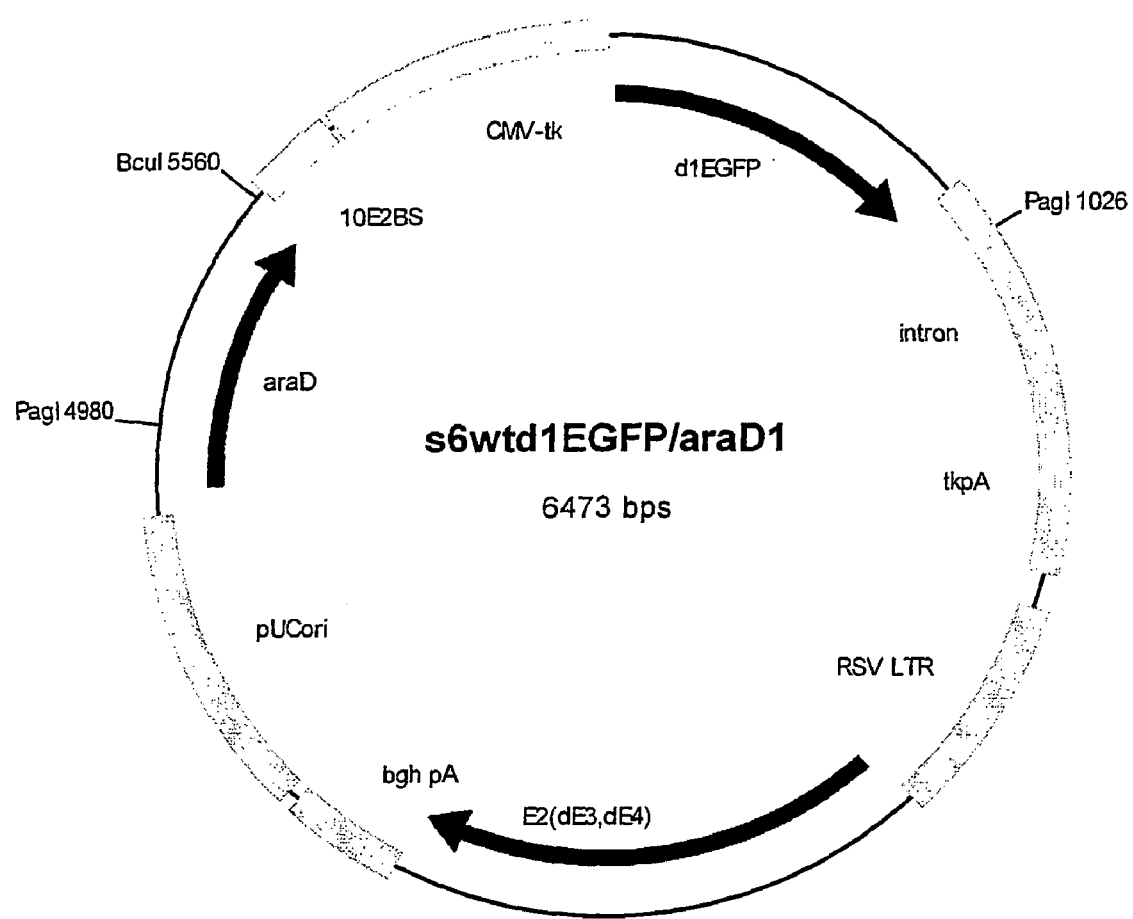
Figure 6:
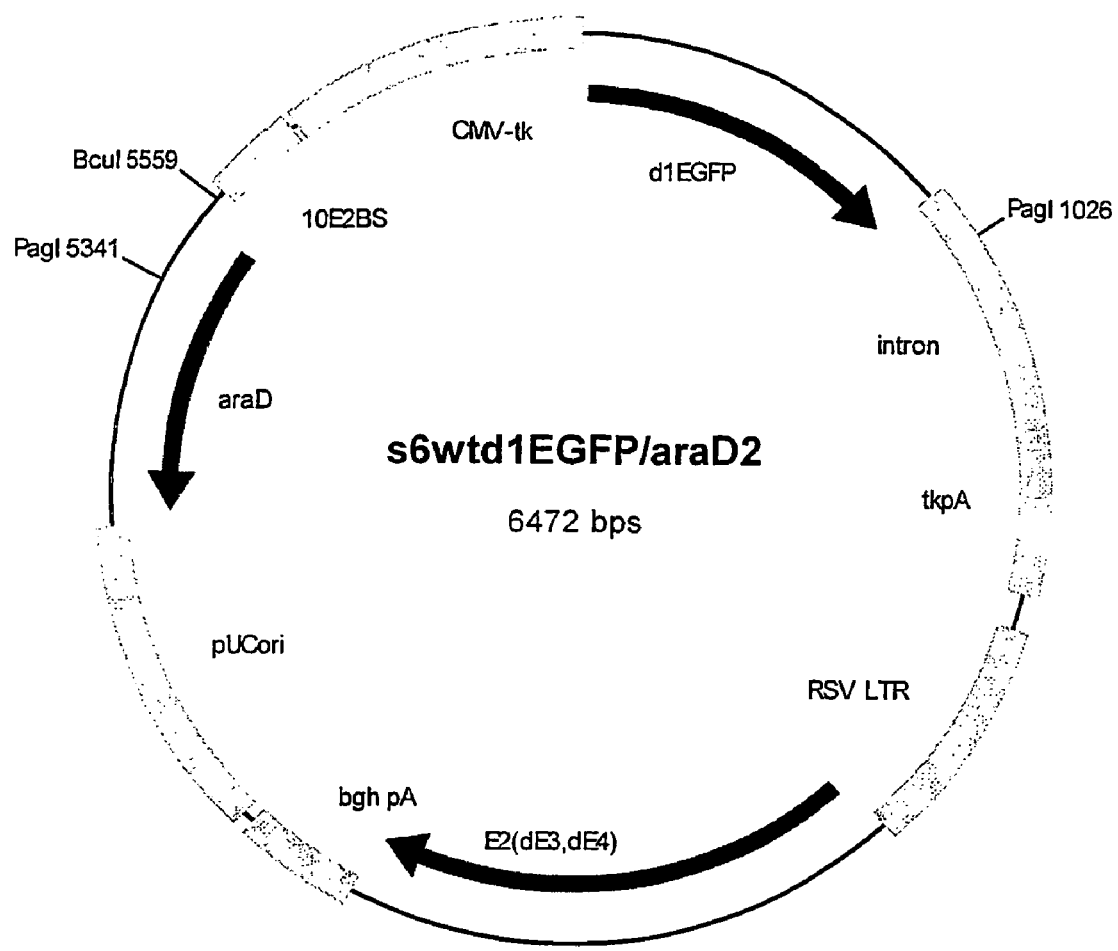

The ligation mixtures were transformed into an E. coli AG1 ΔaraD strain (see Example 3) and plated onto dishes containing M9 media supplemented with 2% L-arabinose and incubated at 37° C. for 36 hours. Colonies were first analyzed with colony PCR, after which the DNA was isolated and digested with different restriction enzymes. The cloning resulted in plasmids S6wtd1EGFP/araD1, S6wtd1EGFP/araD2, respectively, are shown in FIGS. 5 and 6.

Figure 7:
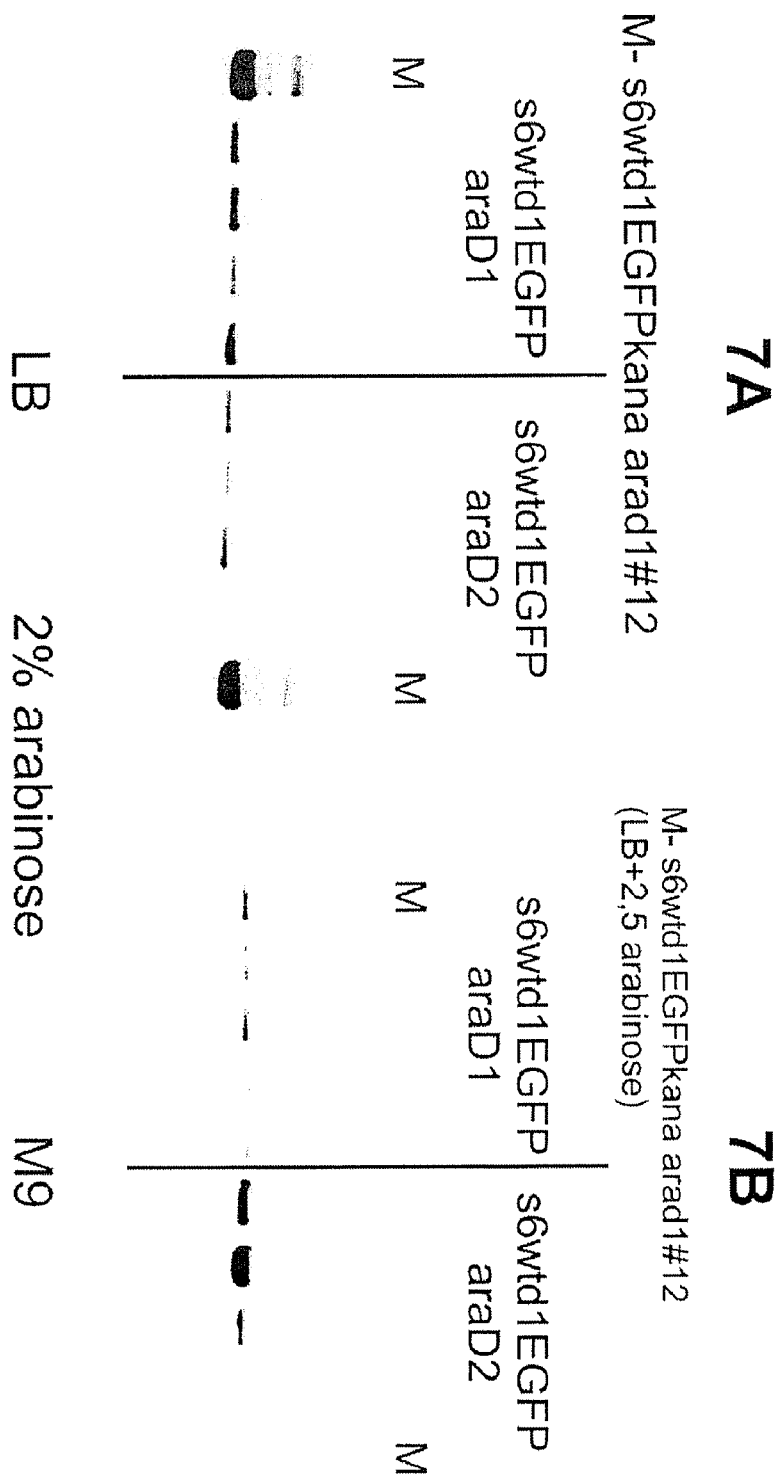
FIGS. 7A and 7B shows the electrophoretic analysis of the plasmid DNA of the S6wtd1EGFP/araD1 (7A) and S6wtd1EGFP/araD2 (7B) extracted from the E. coli strain AG1 delta araD grown in different media.

The bacterial colonies containing S6wtd1EGFP/araD1 and S6wtd1EGFP/araD2 were grown in two different media: LB supplemented with 2.5% L-arabinose and M9 supplemented with 0.2% L-arabinose at 37° C. with vigorous shaking. The cells were harvested and the plasmid DNA was extracted from the cell using QIAprep Spin Miniprep Kit (QIAGEN) and analysed by agarose gel electrophoresis (FIGS. 7A and 7B, respectively).

Figure 8:
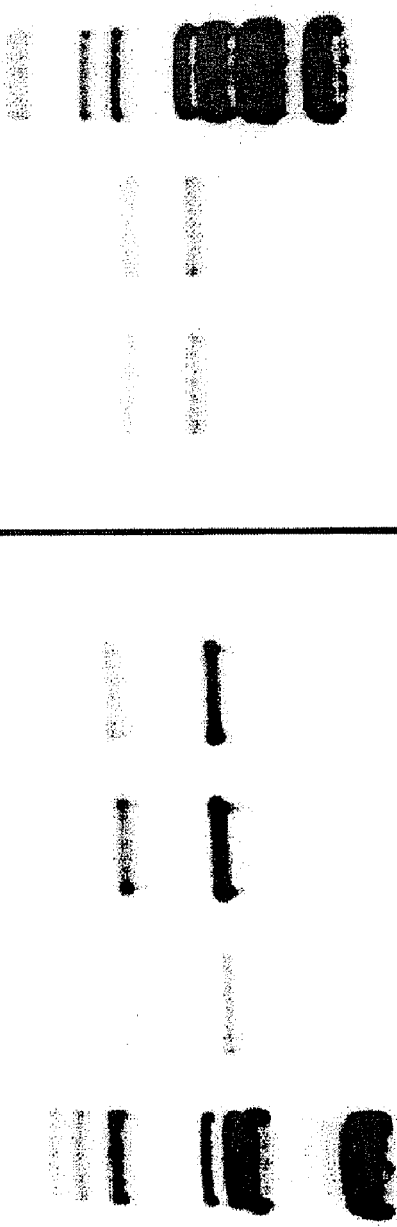
FIG. 8 shows the restriction pattern analysis of the plasmid DNA of the S6wtd1EGFP/araD1 and S6wtd1EGFP/araD2 extracted from the E. coli strain AG1delta araD

The plasmid DNA samples from cultures in LB and M9 media were analysed by agarose gel electrophoresis before and after digestion with restriction endonuclease PagI (Fermentas, Lithuania), (FIG. 8). The predicted sizes of the fragments obtained in the PagI digestion were 3954 and 2519 bp for S6wtd1EGFP/araD1 and 4315 and 2157 bp for S6wtd1EGFP/araD2. Lambda DNA digested with Eco91I (M15 in FIG. 8C) and lambda DNA digested with EcoRI/HindIII (Fermentas, Lithuania) (M3 in FIG. 8C) were used as molecular weight markers. All analyzed bacterial clones contained the correct plasmid in the restriction enzyme analysis, but the DNA yield was very low when the plasmids were grown in LB media. Two of the analyzed bacterial clones from four S6wtd1EGFP/araD2 clones (#13 and #14 in FIG. 8B) had higher growth rate when grown in M9 media supplemented with 0,2% L-arabinose (FIGS. 7 and 8), which resulted in higher plasmid yield per culture.

Further analysis of these two clones with improved growth was performed. These two plasmids had the same structure as the other plasmids as judged by restriction analysis. The plasmids were extracted from the bacteria and further characterized by sequencing the araD gene locus. The araD locus sequence of clone #13 (SEQ ID NO. 18; SEQ ID NO. 19) indicated that araD gene coding sequence carries a STOP codon instead of a codon for Glutamine in position 8 of L-ribulose-5-phosphate 4-epimerase. This mutation resulted from the replacement of Cytidine in codon 8 of L-ribulose-5-phosphate 4-epimerase (araD coding sequence) (5'-CAG-3') with the Thymidine, resulting in a STOP codon (5'-TAG-3'). The plasmid carrying such a mutation in araD gene effectively provided the ability to grow in the selective medium in the presence of L-arabinose although the coding sequence contains the STOP codon. It has been demonstrated that the STOP codon UAG is effectively read through by the ribosomes of Escherichia coli, when such a STOP is in the beginning of the coding sequence [for reference, see review Murgola, E. J., Annu. Rev. Genet. 19 (1985) 57-80]. Without binding by the theory, we hypothesized that the high yield of the plasmid, which is an indication of rapid uninhibited growth of the bacteria, requires an optimal concentration of the araD gene product L-ribulose-5-phosphate 4-epimerase.

The analysis of clone #14 araD locus sequence indicated that the araD coding sequence is perfect as predicted. However, the sequence rearrangements near the araD promoter covering the E2 protein binding sites were observed (see FIG. 13, SEQ ID NO. 18). These data suggested additionally that such rearrangements near the promoter might result in the down-regulation of the promoter activity, therefore the level of the araD product.

EXAMPLE 2

Cloning of Mutated araD Selection Plasmids

For cloning of mutated araD selection constructs plasmid p3hCG (FIG. 14) carrying kanamycin resistance [transposon Tn5 derived kanamycin resistance marker (neo) gene] was cleaved with the restriction endonucleases BcuI and HindIII, the ends were filled in using Klenow Fragment (Fermentas, Lithuania) and the fragment with the size of 4647 bp was purified from the gel after agarose gel electrophoresis. The pMB1 origin of replication and the araD sequence carrying the C to T mutation, which results in a STOP codon in position 8 of the araD gene coding sequence, was excised from the plasmid paraDMgB (FIG. 15) with the restriction endonucleases BcuI and Eco52I, the ends were filled in using Klenow Fragment (Fermentas, Lithuania), and the DNA 5'-termini were dephosphorylated with Calf Intestine Alkaline Phosphatase (CIAP; Fermentas, Lithuania). The fragment with the size of 1532 bp was purified from the gel after agarose gel electrophoresis and ligated with the 4647 bp fragment obtained above. Escherichia coli AG1 araD deficient strain was transformed with this ligation mixture and plated onto agar plates containing selective M9 medium with 0.5% yeast extract, 2% L-arabinose and 25 µg/ml of kanamycin. The colonies were inspected 24 hours after the plating and showed that the size of the colonies was uniform. The plasmids were extracted from the bacteria and further characterized by sequencing of the araD gene locus.

The cloning resulted in plasmids p3araD1hCG and p3araD2hCG, which are shown in FIGS. 16 and 17, respectively. According to the sequence analysis, the bacteria contained un-rearranged plasmids with the mutation C to T in codon 8 (p3araD1hCG; FIG. 16; p3araD2hCG, FIG. 17).

When this experiment was repeated with the wild type sequence and transformed plates were inspected 24 hours after the transformation, the result was different. Two types of colonies were observed: first, large size colonies, and small colonies, which had a retarded growth. The sequence analysis of these plasmids indicated that araD gene coding sequence carries a STOP codon instead of a codon for glutamine (plasmid #3A, araD2) or the mutation had occurred in the Shine-Dalgarno sequence in the ribosomal binding site (AGGAG was replaced with AGTAG) (plasmid #2A, araD2). Plasmid #7 (araD1) had the correct sequence in all araD gene locus regions, however, the bacteria grew very slowly and resulted in a 10 times lower plasmid yield when were grown in liquid media.

EXAMPLE 3

Construction of Arabinose Sensitive ΔaraD
Escherichia Coli Strains

Three E. coli strains, DH5alpha T1, AG1 and JM109, were used to construct ΔaraD mutants. The araD gene in E. coli genome was disrupted using the method described by Datsenko and Wanner [PNAS 97 (2000) 6640-6645]. This method exploits a phage λ Red recombination system. Briefly, the strategy of this system is to replace a chromosomal sequence with a selectable antibiotic resistance gene that is generated by PCR by using primers with homology extensions. This is accomplished by Red-mediated recombination in these flanking homologies.

For transformation of the pKD46 (Datsenko and Wanner, supra), which encodes the phage A recombination system, *E. coli*, the cells were made chemically competent using RF1 and RF2 solutions:

| RF1 100 ml | |
|---|---|
| RbCl 1 | 1.2 g |
| $MnCl_2 \cdot 4H_2O$ | 0.99 g |
| 1 M KAc pH 7.5 | 3 ml |
| $CaCl_2 \cdot 2H_2O$ | 0.15 g |
| Glycerol | 15 g |
| pH 5.8 | (add $CH_3COOH$) |

| RF2 100 ml | |
|---|---|
| 0.5 M MOPS | 2 ml |
| RbCl | 0.12 g |
| $CaCl_2 \cdot 2H_2O$ | 1.1 g |
| Glycerol | 15 g |
| pH 6.8 | (add NaOH) |

The cells were grown in 2 ml of LB medium to $OD_{600}$ 0.2-0.5. The culture was centrifuged and the pellet was resuspended in 1 ml of RF1. The mixture was kept on ice for 10 min and centrifuged. The pellet was suspended in 100 µl of RF2 and the suspension was kept on ice for 30-45 min. Approximately 50 ng of pKD43 was added and the cells were kept on ice for additional 30 min followed by heat shock of 5 min at 37° C. After incubation for 10 min on ice 900 µl of SOB medium was added to the transformed cells and the mixture was incubated at 37° C. for one hour. Cells were plated on LB medium containing ampicillin (100 µg/ml). The colonies were picked from the transformation plates and grown in 2 ml of the same medium to $OD_{600}$ of approximately 1 and glycerol stocks were made (2 ml culture+0.6 ml 50% glycerol). The stocks were stored at –80° C.

For disruption of the araD gene a linear PCR product which contains kanamycin resistance gene was generated. Plasmid pKD13 (Datsenko and Wanner, PNAS vol. 97, no 12, June 2000) was used as the PCR template. Primers used were ara(pr1) and ara(pr4):

ara(pr1)
5'-CTCAAACGCCCAGGTATTAGAAGCCAAC-CTGGCGCTGCCAAAACACGTGTAG GCTGGAGCT-GCTTC 3' (SEQ ID NO. 12)

ara(pr4)
5'-GGTTTGATCACAAAGACGCCGCGCTCGC-GATCAACGGCGCATTCCGGGGAT CCGTCGACC 3' (SEQ ID NO. 13)

These primers have the complement sequences with pKD13 for annealing in PCR and with the araD gene for homologous recombination.

The PCR reaction mixture was as follows: PFU native buffer (5 µl), 10 mM dNTP (5 µl), primer ara(pr1) 10 µM (1 µl), primer ara(pr4) 10 µM (1 µl), pKD13 100 ng (2 µl), DMSO (4 µl), PFU 2.5 U (1 µl), and mQ water up to 50 µl.

The PCR procedure was as follows: denaturation 45 s, 96° C., annealing 45 s, 50° C., synthesis 2 min 30 s, 72° C., 25 cycles. The PCR product obtained was 1.4 kb.

Five reactions were performed simultaneously; the DNA was purified from 2% agarose gel using Ultrapure purification Kit (MoBio Labotratories Inc.) and eluted with 60 p, of water. The DNA was concentrated with ethanol precipitation and dissolved in 5 p, of water. The final concentration was 0.6 µg/µl. An aliquot of 1.5 µl was used in one electroporation.

The PCR product was electroporated into DH5alpha T1 pKD46, AG1 pKD46 (Datsenko and Wanner, supra), and JM109 pKD46 *E. coli* cells. First, 200 ml of YENB medium containing 10 mM of L-arabinose for the induction of the recombination system and 100 µg/ml ampicillin was inoculated with an overnight culture of DH5alpha T1 pKD46, AG1 pKD46, and JM109 pKD46 *E. coli* cells. The cultures were grown at 30° C. to $OD_{600}$ 0.8 (DH5alpha T1 and JM109) and 0.6 (AG1). The bacteria was collected by centrifugation at 4,000 g for 10 min at 4° C., washed twice with 20 ml of sterile water and once with 20 ml of sterile water containing 10% glycerol. The cells were suspended in 300 µl water containing 10% glycerol. 40 p, of competent cells were used in one electroporation.

The electroporation was performed with BioRad *E. coli* Pulser using 0.2 cm cuvettes and 2.5 kV. The purified PCR product (1.5 µl) was added to the competent cells, kept on ice for 1 min, and immediately after the electroporation, 2 ml of warm SOB medium was added to the cells and the mixture was incubated at 37° C. for 1 hour. The cells were plated on LB medium containing kanamycin (25 µg/ml). 100 µg of large kanamycin resistant plasmid (GTU-MultiHIV C-clade) was used as a positive control, no plasmid was added to the negative control. The transformation efficiency was 106 for AG1 and $10^7$ for JM109 for positive control. There were no colonies on the negative control plate, 215 colonies were obtained on JM109+PCR product plate, 70 colonies on AG1+PCR product plate and 50 colonies on DH5alpha T1+PCR product plate.

EXAMPLE 4

Testing of the *E. coli* DH5alpha T1 ΔaraD, AG1ΔaraD and JM109ΔaraD Strains

The colonies obtained from the electroporation as described in Example 2 were tested for the presence of kanamycin resistance gene by colony PCR using primers araVIisF (5'CGGCACGAAGGAGTCAACAT 3'; SEQ ID NO. 14) and araVIis R (5' TGATAGAGCAGCCGGTGAGT 3'; SEQ ID NO. 15) which contain annealing sites on the araD gene near the insertion site. A PCR product of 272 bp was expected from the *E. coli* DH5alpha T1, AG1 and JM109 strains without insertion in araD and a 1545 bp product, if the PCR product had been inserted in the araD gene. Three colonies of DH5alpha T1 ΔaraD, nine colonies of AG1ΔaraD and 14 colonies of JM109ΔaraD out of 15 were checked and each gave the 1545 bp product. It was therefore concluded that these strains contained the kanamycin resistance gene insertion.

To confirm the insertion of kanamycin gene another colony PCR was performed using primers kanaSF (5'TCAGATCCT-TGGCGGCAAGA3'; SEQ ID NO. 16) and araVR (5'TG-TAATCGACGCCGGAAGGT3'; SEQ ID NO. 17). These primers produce a 435 bp product, if the kanamycin resistance gene has been inserted into the araD gene. Six colonies from AG1ΔaraD and JM109ΔaraD strains and three colonies of DH5alpha T1 ΔaraD strains were tested and all gave the correct product.

Six colonies of AG1ΔaraD and JM109ΔaraD, and three colonies of DH5alpha T1 ΔaraD were plated on LB medium containing 25 µg/ml of kanamycin and incubated at 37° C. overnight to eliminate the pKD46 plasmid, which has a temperature sensitive replication origin. The cells were tested for ampicillin sensitivity by replica plating on LB medium and LB medium containing ampicillin. None grew on the medium containing ampicillin and it was concluded that the bacteria does not contain the pKD46 plasmid any more.

The arabinose sensitivity was tested on the produced AG1ΔaraD and JM109ΔaraD strains. One colony of AG1ΔaraD and one colony of JM109ΔaraD were each inoculated into 2 ml LB. The cultures were grown for 8 hours, diluted 1:100 into M9 medium containing 0.2% glycerol, 25 μg/ml kanamycin, 0.01% thiamine (0.05% proline for JM109ΔaraD) and different concentrations of L-arabinose were added in the growth medium. The cultures were grown overnight at 37° C. in shaker incubator and $OD_{600}$ was measured (Table 1).

The colonies from the transformation plates were inoculated into 2 ml of M9 medium containing 0.5% yeast extract and 25 μg/ml kanamycin+0.01% thiamine+L-arabinose (2% and 0.2%).

The cultures were incubated at 37° C. for 17 hours. Then the $OD_{600}$ was measured to quantitate the cell density and the plasmid DNA was extracted with Qiagen Miniprep Kit. Coefficient 2.8 ($OD_{600}$/ml) was used for mini-prep isolation to get comparable results. The results are shown in Table 2.

DNA concentration was measured with spectrophotometer as OD at 260 nm. For microscopic analysis a drop of bacterial culture was applied on glass slide and covered with cover slip. The culture was visually inspected at a 100× magnification with an objective in oil immersion.

TABLE 2

Plasmid DNA yield of ΔaraD strains

| Strain | L-arabinose (%) | $OD_{600}$ | Plasmid DNA conc. (μg/μl) | Plasmid DNA yield (μg per ml of culture) | Appearance in microscope |
|---|---|---|---|---|---|
| AG1ΔaraD | 2 | 7.6 | 0.039 | 5.3 | no filaments |
| AG1ΔaraD | 0.2 | 5.8 | 0.057 | 5.9 | no filaments |
| JM109ΔaraD | 2 | 4.9 | 0.043 | 3.8 | very few filaments |
| JM109ΔaraD | 0.2 | 4.3 | 0.038 | 2.9 | very few filaments |
| DH5αT1ΔaraD | 2 | 6.6 | 0.017 | 3.5 | no filaments |
| DH5αT1ΔaraD | 0.2 | 6.4 | 0.016 | 3.4 | no filaments |

TABLE 1

Testing of arabinose sensitivity.

| L-arabinose % | AG1ΔaraD $OD_{600}$ | JM109ΔaraD $OD_{600}$ |
|---|---|---|
| 0 | 3.2 | 1.9 |
| 0.1 | 0.03 | 0.03 |
| 0.2 | 0.030 | 0.026 |
| 0.5 | 0.030 | 0.020 |
| 1 | 0.024 | 0.025 |
| 2 | 0.017 | 0.021 |

As can be seen from Table 1, as low amount as 0.1% of L-arabinose is enough to inhibit the growth of the ΔaraD strains of the invention.

The arabinose sensitivity was further tested on AG1ΔaraD, DH5alphaT1 ΔaraD and JM109ΔaraD as above but using lower concentrations of L-arabinose. The results are given in FIG. 18. As can be seen in FIG. 18, as low an amount as 0.0005% of L-arabinose is enough to inhibit the growth of the ΔaraD strains of the invention.

Additionally the L-arabinose sensitivity was tested in M9 and yeast extract medium with different glucose and arabinose concentrations (0.2% glucose, 0.2% arabinose, 2% arabinose). The cultures were incubated at 37° C. in a shaker incubator overnight. Then the $OD_{600}$ was measured to quantitate the cell density. The results are given in FIG. 19.

Both concentrations of arabinose (0,2% and 2%) inhibited the growth of the ΔaraD strains of the invention. However, the growth of strains with intact araD gene was not inhibited.

Additionally the plasmid DNA yield of the ΔaraD strains was tested. Plasmid S6wtd1EGFParaD2 prepared in Example 1 was transformed into AG1ΔaraD and JM109ΔaraD strains. Competent cells were prepared with RF1 and RF2 solutions as described in Example 3.

According to these results 0.2% L-arabinose is sufficient for obtaining the plasmid copy number at the same level as with 2% arabinose.

For this plasmid AG1ΔaraD seems to be better, because the plasmid yield is somewhat higher and cell densities also.

EXAMPLE 5

Generation of an *Escherichia coli* Strain with Additional Mutations Within the Genes Potentially Encoding L-Ribulose-5-Phosphate 4-Epimerase

*E. coli* chromosome contains two additional coding sequences for L-ribulose-5-phosphate 4-epimerases in different operons. The ulaF and sgbE genes from L-ascorbate degradation pathway encode the genes with epimerase activity (Wen Shan Yew, Jhon A. Gerit, J. Bacteriol. 184 (2002) 302-306. In order to increase the stringency of the selection and to avoid or knock out the possible adaptation mechanisms of *E. coli* strains due to other genes with epimerase activity, the coding sequences of the UlaF and SgbE genes in *E. coli* genome were interrupted. Such adaptation mechanisms could occur in long-term plasmid production under suitable conditions.

The UlaF and SgbE genes in *E. coli* strains DH5alphaT1ΔaraD and AG1ΔaraD were disrupted using the phage λ Red recombination system as described in Example 3.

First, the kanamycin-resistant gene in *E. coli* AG1ΔaraD and DH5aT1ΔaraD strains was eliminated. FLP recombinase expression plasmid pKD20 (Datsenko and Wanner, supra) is ampicillin resistant and temperature-sensitive. Kanamycin-resistant mutants were transformed with pCP20 (kana-mycin-resistant gene is FRT-flanked), and ampicillin-resistant transformants were selected at 30° C. (48 hours), after which the same colonies were purified non-selectively at 42° C. (24 hours twice). Then they were tested for loss of kanamycin and ampicillin resistances.

The inactivation of the chromosomal ulaF gene (SEQ ID NO. 20) by the phage λ Red recombination system was performed using the primers ulaFylem and ulaFalum:
ulaFylem
CAGCAGGTATTTGAAGCCAACATG-GAGCTGCCGCGCTACGGGCTGGTGTAG-GCTGGAGCTGCTTC (SEQ ID NO. 21)
ulaFalum
AAACGGCTGCGGAATTAGACCAGT-TATCTCCCGAGGAAGGAAA TTAATTCCGGGGATC-CGTCGACC (SEQ ID NO. 22)

A lot of colonies were observed on both transformation plates. Fifteen colonies obtained from the electroporation were tested for the presence of the kanamycin resistance gene by colony PCR using primers ulaFvalis R and ulaFvalisF:
ulaFvalis R
AAACGGCTGCGGAATTAGACC (SEQ ID NO. 23)
ulaFvalisF
GCCGTACCTGATTGAGATGTGGAG (SEQ ID NO. 24)

These primers contain annealing sites on the U/aF gene near the insertion site. A PCR product of 864 bp was expected from the E. coli DH5alphaT1ΔaraD and AG1ΔaraD strains without insertion in U/aF and a 1527 bp product, if the PCR product had been inserted in the U/aF gene. To confirm the insertion of the kanamycin gene another colony PCR was performed using primers ulaFvalis R (SEQ ID NO 23) and kanaSF (SEQ ID NO 16).

These primers produce a 428 bp product, if the kanamycin resistance gene has been inserted into the UlaF gene. Four colonies from AG1ΔaraDΔulaF and DH5alphaT1ΔaraDΔulaF strains were tested and all gave the correct product. One colony from each strain was used further.

The elimination of the kanamycin-resistant gene in E. coli AG1ΔaraDΔulaF and DH5alphaT1ΔaraDΔulaF strains was performed as described above. The inactivation of the chromosomal sgbE gene (SEQ ID NO. 25) by the phage A Red recombination system was performed as described in Example 3 The primers used were sgbEalum and sgbEylem
sgbEalum
CGTTACAGCCAAGGAACATATCAATTCG-TAGTGCCGGGGCGATG AAGAATTCCGGGGATC-CGTCGACC (SEQ ID NO. 26)
sgbEylem
GCAGGAGGCTGGATTTATATGTTAGAG-CAACTGAAAGCCGACGTGGTGTAGGCTG-GAGCTGCTTC (SEQ ID NO. 27)

A lot of colonies were observed on both transformation plates. Fifteen colonies obtained from the electroporation were tested for the presence of kanamycin resistance gene by the colony PCR using primers sgbEvalis R and sgbEvalisF:
sgbEvalisR
CGGCGTTACAGCAAGGAACATATC (SEQ ID NO. 28)
sgbEvalisF
ATTGAAGCGCGTATGCAGGAGG (SEQ ID NO. 29)

A PCR product of 792 bp was expected from the E. coli DH5alpha T1ΔaraDΔulaFΔsgbE and AG1ΔaraDΔulaFΔsgbE strains without insertion in SgbE and a 1413 bp product, if the PCR product had been inserted in the SgbE gene. To confirm the insertion of kanamycin gene another colony PCR was performed using primers sgbEvalis R (SEQ ID NO. 28) and kanaSF (SEQ ID NO. 16):

Fifteen colonies from both strains were tested and four gave the correct product.

The arabinose sensitivity was tested on the E. coli DH5alphaT1 ΔaraDΔulaFΔsgbE and AG1ΔaraDΔulaFΔsgbE strains produced and compared to those of E. coli DH5alphaT1ΔaraD and AG1ΔaraD strains. One colony of each strain was inoculated into 2 ml of M9 medium containing 0.5% yeast extract, 25 µg/ml of kanamycin, 0.2% glucose only or 0.2% or 2% L-arabinose, respectively. The results are shown in Table 3.

TABLE 3

Testing of arabinose sensitivity

| Strain | $OD_{600}$ Glc | $OD_{600}$ Glc + 0.2% L-arabinose | $OD_{600}$ Glc + 2% L-arabinose |
|---|---|---|---|
| AG1 ΔaraD | 7.3 | 0.82 | 0.26 |
| DH5alphaT1 ΔaraD | 7.7 | 0.95 | 0.35 |
| AG1ΔaraD ΔulaFΔsgbE | 8.3 | 0.82 | 0.35 |
| DH5alphaT1 ΔaraDΔulaF ΔsgbE | 7.5 | 0.75 | 0.28 |

As can be seen from Table 3, there were no essential differences in the arabinose sensitivity of the strains of the invention. Similarly, when the plasmid DNA yield of the ΔaraD and ΔaraDΔulaFΔsgbE strains was tested as described in Example 3 (the results are not shown), no differences were found between E. coli AG1ΔaraD and AG1ΔaraDΔulaFΔsgbE or DH5alphaT1ΔaraD and DH5alphaT1ΔaraDΔulaFΔsgbE strains.

EXAMPLE 6

Stability of S6wtd1EGFP/araD2

An important feature of the vaccination vector is the stability during propagation in bacterial cells. To test the stability of S6wtd1EGFP/araD2 in bacteria the plasmid was transformed into the E. coli AG1ΔaraD and JM109ΔaraD strains prepared in Example 3 and the intactness of the vector was followed by the plasmid DNA analysis during four generations.

Figure 9:
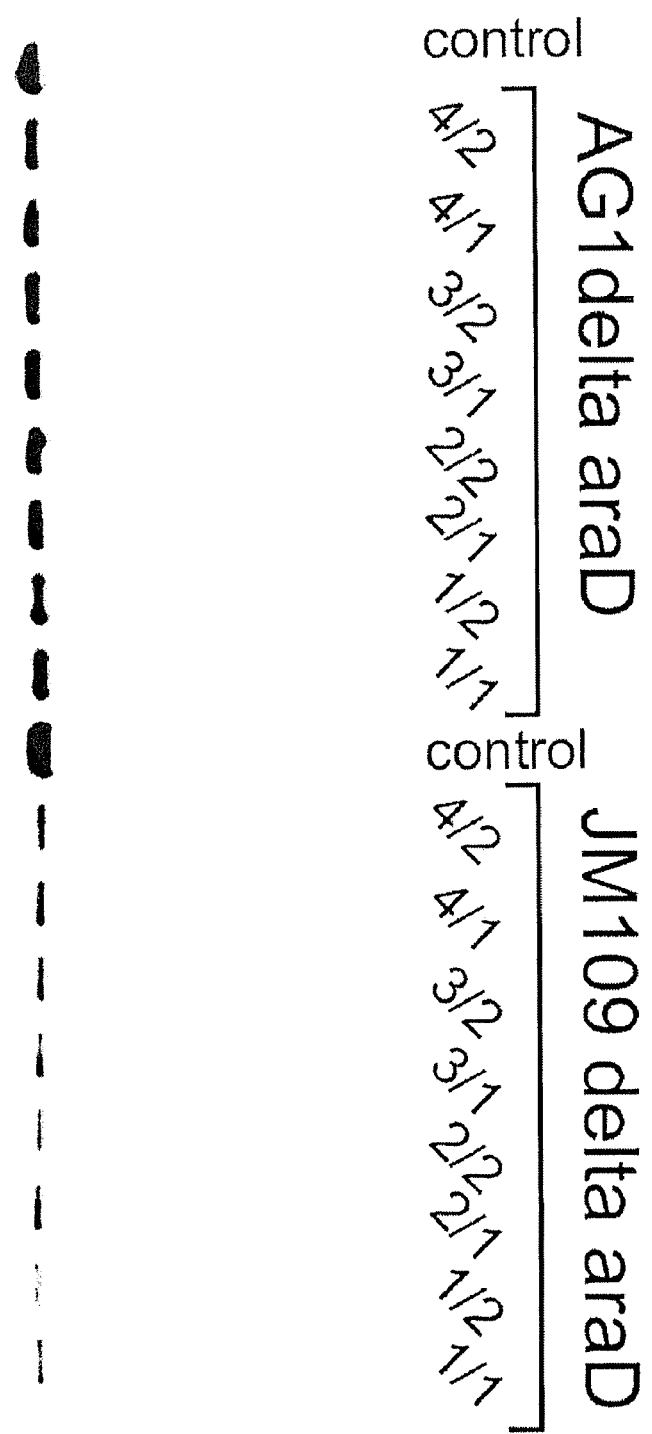
FIG. 9 shows the electrophoretic analysis of the S6wtd1EGFP/araD2 in stability assay.

The plasmid S6wtd1EGFP/araD2 was mixed with competent E. coli AG1ΔaraD and JM109ΔaraD cells and incubated on ice for 30 minutes. Subsequently, the cell suspension was subjected to a heat-shock for 3 minutes at 37° C. followed by a rapid cooling on ice. One milliliter of LB medium was added to the sample and the mixture was incubated for 45 minutes at 37° C. with vigorous shaking. Finally, a portion of the cells was plated onto M9 medium dishes containing 0.5% yeast extract, 2% L-arabinose and 25 µg/ml of kana-mycin. On the next day, the cells from one colony were transferred onto the new dish containing the same medium. This procedure was repeated until four passages of bacteria had been grown. Two colonies from each passage of both bacterial strains were used to inoculate of 2 ml of M9 medium containing 0.5% yeast extract, 2% L-arabinose and 25 µg/ml of kanamycin incubated overnight at 37° C. with vigorous shaking. The cells were harvested and the plasmid DNA was extracted from the bacteria using QIAprep Spin Miniprep Kit (QIAGEN). The plasmid DNA samples before (FIG. 9) and after the digestion with restriction endonuclease HindIII (FIG. 10) (Fermentas, Lithuania) were analyzed by agarose gel electrophoresis in comparison with the original S6wtd1EGFP/araD2 DNA used for transformation (as control in FIGS. 9 and 10). Lambda DNA digested with EcoRI/

Figure 10:
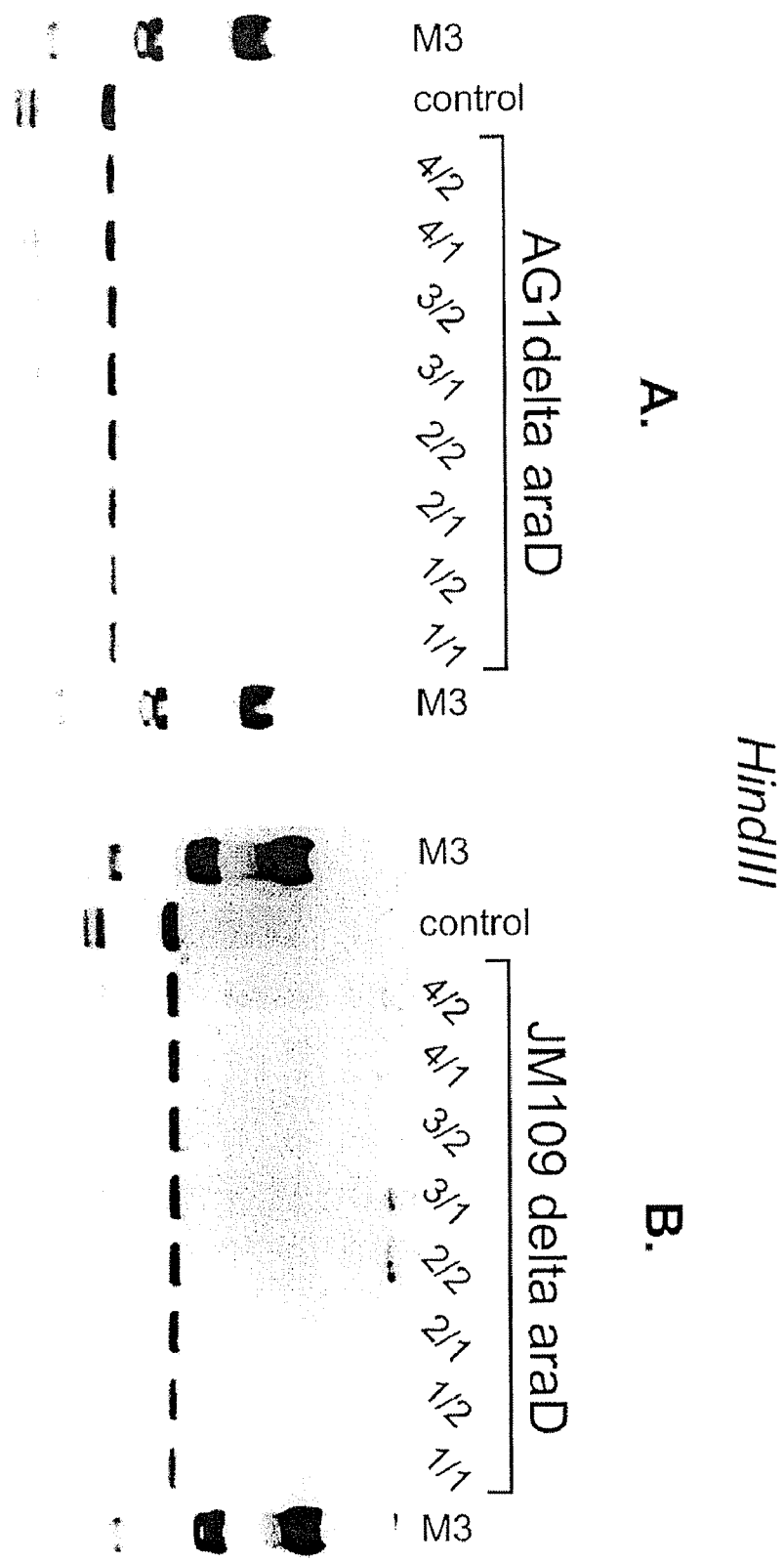
FIGS. 10A and 10B shows the restriction pattern analysis of the S6wtd1EGFP/araD2 in stability assay.

HindIII (Fermentas, Lithuania) was used as a molecular weight marker (M3 in FIG. 10).

Samples were digested with HindIII as shown in FIG. 10A for *E. coli* AG1ΔaraD and in FIG. 10B for JM109ΔaraD strain, patterns identical to the original S6wtd1EGFP/araD2 plasmid DNA were observed. The predicted sizes of the fragments resulted by HindIII digestion are 3274, 1688 and 1510 bp. It can be concluded that the vaccination vector S6wtd1EGFP/araD2 is stable when propagated in *E. coli* AG1ΔaraD and JM109ΔaraD strains.

EXAMPLE 7

Comparison of an Antibiotic Selection System with the L-Arabinose Selection System of the Invention In the comparison of an antibiotic selection system with the L-arabinose selection system of the invention the following growth media were used.

For *E. coli* AG1 carrying plasmid p2 MG C #11:
Medium 1: M9 medium plus 0.5% yeast extract, 0.2% glucose and 25 μg/ml of kanamycin (selective medium);
Medium 2: M9 medium plus 0.5% yeast extract and 0.2% glucose (non-selective medium);
Medium 3:
M9 medium plus 0.5% yeast extract, 0.2% L-arabinose and 25 μg/ml of kanamycin; (selective medium); and
Medium 4: M9 medium plus 0.5% yeast extract and 0.2% L-arabinose (non-selective medium).

For *E. coli* AG1ΔaraD carrying paraD MG C #145:
Medium 5:
M9 medium plus 0.5% yeast extract, 0.2% L-arabinose and 25 μg/ml of kanamycin (selective medium); and
Medium 6:M9 medium plus 0.5% yeast extract, 0.2% glucose and 25 μg/ml of kanamycin (non-selective medium).

The plasmids p2 MG C #11 (FIG. 20) and paraD MG C #145 (FIG. 21) were transformed into *E. coli* AG1 and into *E. coli* AG1ΔaraD carrying the mutation C to T in codon 8. The transformed bacterial colonies were grown at 37° C. overnight in an incubator. Next morning the colonies were inoculated into the selective and non-selective liquid media as indicated above. The inoculated cultures were grown in a shaker in 2 ml of the respective medium until they reached the stationary phase, and the density of the cultures was measured at $OD_{600}$. The plasmid was extracted from the cultures and the plasmid DNA yield was determined by the measurement of the plasmid DNA at 260 nm. The plasmid yield was calculated on the basis that 50 μg yields to an optical density of 1 at 260 nm.

Then an aliquot of 20 μl from the stationary cultures was inoculated into fresh medium (dilution 100 times), and the cultures were grown until stationary phase (8-12 hours). The density of the cultures was measured at $OD_{600}$, the plasmid was extracted and the yield was determined, and again an aliquot was inoculated into 2 μl of the liquid medium. This procedure was repeated 7 times (preparations 1 to 7). The results of the experiment are provided in Table 5 below.

TABLE 5

Comparison of an antibiotic selection system with the L-arabinose selection system of the invention

| Medium number/preparation number | $OD_{600}$ | Amount of plasmid DNA per 1 ml culture |
|---|---|---|
| 1/1 | 6.215 | 6.35 μg |
| 1/7 | 3.278 | 2.3 μg |
| 2/1 | 6.652 | 6.15 μg |
| 2/7 | 5.133 | 0.65 μg |
| 3/1 | 7.317 | 10.9 μg |

TABLE 5-continued

Comparison of an antibiotic selection system with the L-arabinose selection system of the invention

| Medium number/preparation number | $OD_{600}$ | Amount of plasmid DNA per 1 ml culture |
|---|---|---|
| 3/7 | 3.046 | 1.6 μg |
| 4/1 | 6.874 | 6 μg |
| 4/7 | 4.634 | 0.75 μg |
| 5/1 | 7.271 | 6.45 μg |
| 5/7 | 7.014 | 5.15 μg |
| 6/1 | 6.131 | 5.3 μg |
| 6/7 | 6.031 | 4.4 μg |

It can be concluded from these data that a plasmid carrying the kanamycin resistance gene and conferring *E. coli* the resistance in the presence of kanamycin is lost in the consecutive dilution/growing steps of the culture under the non-selective as well as under selective conditions. The yield of the plasmid from 1 ml culture drops 3 times under the selective conditions and 10 times under the non-selective conditions at the seventh round of dilution (preparations 1/1 vs. 1/7 and 2/1 vs. 2/7, respectively, in Table 5). The same basic result is obtained, when the carbon source for *E. coli* carrying a plasmid with kanamycin resistance is L-arabinose instead of glucose (preparations 3/1 vs. 3/7 and 4/1 vs. 4/7, respectively, in Table 5). However, when the araD selection system of the invention is used in the plasmid, the plasmid DNA yield is high under both selective (preparation 5/1 vs. 5/7 in Table 5) and non-selective (preparation 6/1 vs. 6/7 in Table 5) conditions. Both under selective and non-selective conditions the plasmid DNA yield dropped over 7 generations approximately 20%. This indicates clearly that the plasmids carrying araD selection system of the invention are much more stable and grow efficiently under the selective as well as non-selective conditions.

EXAMPLE 8

Fed-Batch Fermentation of AG1ΔaraD S6wtd1EGFP/araD2

Figure 11:
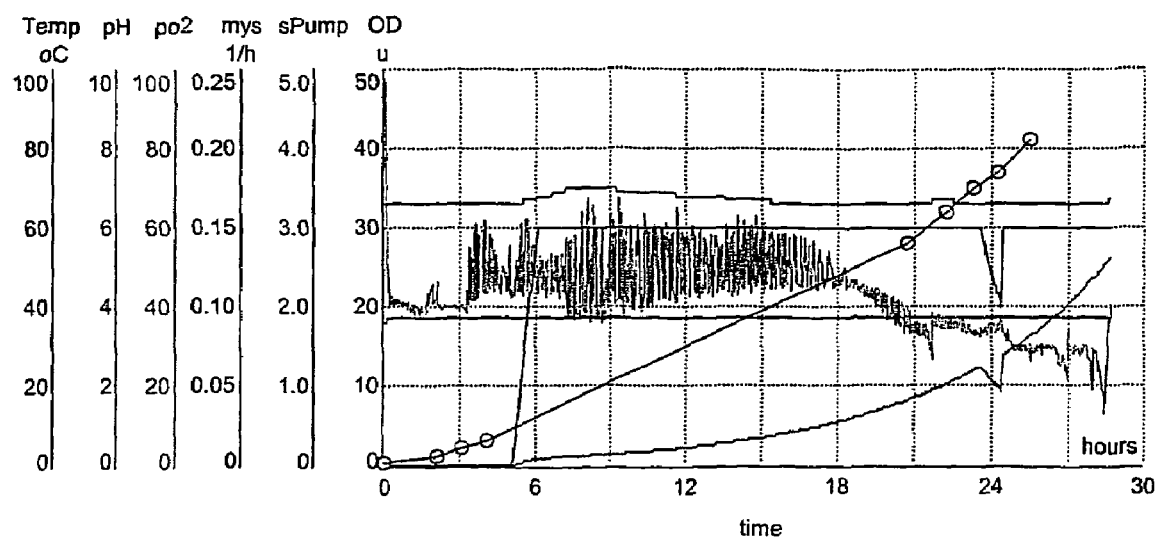
FIG. 11 shows the growth parameters of fed-batch fermentation of AG1ΔaraD S6wtd1EGFP/araD2 measured and registered during fermentation.

The araD gene based selection system was also tested in fed-batch fermentation for the purpose of production of plasmid containing bacteria. A single colony was picked from AG1ΔaraD S6wtd1EGFP/araD2 plate and inoculated into 250 ml M9 medium containing 0.5% yeast extract, 0.2% L-arabinose and 25 μg/ml of kanamycin and incubated overnight at 37° C. with vigorous shaking. After 18 hours the $OD_{600}$ of inoculum was 6.4. 160 ml of inoculum was added to fermentor containing 5 l Fermenter Starting Medium (8 g/l $KH_2PO_4$; 10 g/l NaCl; 5 g/l $NH_4Cl$; 5 g/l yeast extract; 2 g/l L-arabinose; 2 g/l $MgSO_4$, 25 mg/l kanamycin and 0.1 g/l thiamine; pH 6.7 with $NH_4OH$). After 5.5 hours of growth automatic feeding was started with given growth speed of 0.15 $h^{-1}$ (allows carbon-source limited growth) with fermenter feeding medium (300 g/l L-arabinose; 150 g/l yeast extract; 50 mg/l kanamycin; 0.2 g/l thiamine). Feeding speed was controlled by computer according to formulae $F(t)= myS*S_{in}/S_f$ where myS is desired growth rate, $S_{in}$ is the amount of carbon source added to the time point and $S_f$ is carbon source concentration in feeding medium. The growth was followed by measuring $OD_{600}$ and samples for plasmid DNA were taken. The data registered during fermentation is represented in FIG. 11. Fermentation was terminated when 1 l of feeding medium was consumed. Final $OD_{600}$ was 45. The bacterial mass was collected by centrifugation and washed once with 2 l STE buffer. Yield of bacterial biomass was 410 g wet weight. The data for plasmid DNA content is shown in Table 6.

TABLE 6

Plasmid DNA yield during AG1ΔaraD S6wtd1EGFP/araD2 fermentation

| Time | $OD_{600}$ | Plasmid DNA conc. (µg/µl) | Plasmid DNA yield (µg per ml of culture) |
|---|---|---|---|
| Inoculum | 6.4 | 0.04 | 4.6 |
| 4 h | 3.1 | 0.02 | 1.1 |
| 21 h | 28 | 0.1 | 50 |
| 24 h | 37 | 0.13 | 87 |
| 29 h | 45 | 0.14 | 113 |

The data in Table 6 indicate that the L-arabinose selection system works very well at high cell densities. It is probably because more plasmid copies in bacterial cell gives an advantage in the conditions of L-arabinose limitation by enabling the bacterium to use sugar more rapidly.

EXAMPLE 9

Purification of AG1ΔaraD S6wtd1EGFP/araD2

The purification of AG1ΔaraD S6wtd1EGFP/araD2 was performed as follows (FIG. 12):
a) Feeding preparation
Clear lysate was prepared according to Qiagen's Plasmid Purification Handbook, exept RNase was not used.
200g of *E. coli* cell paste was resuspended in 2000 ml of Resuspension Buffer and later equal volumes of P2 and P3 for lysis and neutralization were used. The cell debris was removed by centrifugation at 6000 g for 30 minutes at 4° C. Clear lysate was poured through the paper towel, 1/10 of 10% Triton X-114 (Sigma) was added and solution was left on ice for 1 hour. (Triton X-114 has been shown to effectively reduce the level of endotoxins in protein, Liu et al., Clinical Biochemistry, 1997) After one hour nucleic acids were precipitated with 0,6 volumes of cold isopropanol. Supernatant was decanted and precipitate was stored overnight at −20° C.

b) Plasmid DNA purification

Plasmid DNA purification was performed according to Amersham Pharmacia's three step supercoiled plasmid purification process, where few modifications were adopted.

Step 1. Precipitate was redissolved in 1500 ml TE (10 mM Tris-Cl, 1 mM EDTA; pH 8.0) and loaded for RNA removal and buffer exchange on Sepharose 6 FF (Amersham Pharmacia), previously equilibrated with Buffer A-2M $(NH_4)_2SO_4$, 100 mM Tris Cl, 10 mM EDTA, pH 7.5.

Step 2. Void volume was directed to the PlasmidSelect (Amersham Pharmacia) column (equilibrated with Buffer A) and after washing and elution with Buffer B2 (1,6M NaCl, 2M $(NH_4)_2SO_4$, 100 mM Tris Cl, 10 mM EDTA, pH 7.5), supercoiled plasmid DNA was captured.

Step 3. Eluted plasmid was diluted with five volumes of distilled, deionized water and loaded to SOURCE 30Q (Amersham Pharmacia) equilibrated with buffer C1 (0,4M NaCl, 100 mM Tris Cl, 10 mM EDTA, pH 7.5). After washing, purified plasmid was eluted with Buffer C2 (1 M NaCl, 100 mM Tris Cl, 10 mM EDTA, pH 7.5) and elution peak was collected. Fraction size was 150 ml and it contained 100 mg of endotoxins-free (<10 EU/mg) S6wtd1EGFP/araD2 plasmid.

The invention claimed is:

1. An isolated *E. coli* strain DH5alpha-T1 deficient of the araD gene and ulaF gene.

2. An isolated *E. coli* strain DH5alpha-T1 deficient of the araD gene and sgbE gene.

3. An isolated *E. coli* strain DH5alpha-T1 deficient of the araD gene, ulaF gene and sgbE gene.

4. An isolated *E. coli* strain AG1 deficient of the araD gene and ulaF gene.

5. An isolated *E. coli* strain AG1 deficient of the araD gene and sgbE gene.

6. An isolated *E. coli* strain AG1 deficient of the araD gene, ulaF gene and sgbE gene.

7. A vector comprising a mutated *E. coli* araD gene, wherein said mutated *E. coli* araD gene comprises SEQ ID NO: 1, except that codon 8 of the *E. coli* araD gene has been mutated to encode a stop codon rather than a glutamine.

8. The vector of claim 7, wherein the guanine at nucleic acid position 709 of SEQ ID NO: 1 is substituted with adenine.

9. A vector comprising a mutated *E. coli* araD gene, wherein said mutated *E. coli* araD gene comprises SEQ ID NO: 18, except that codon 8 of the *E. coli* araD gene has been mutated to encode a stop codon rather than a glutamine.

10. The vector of claim 9, wherein the cytidine at nucleic acid position 320 of SEQ ID NO: 18 is substituted with thymidine.

11. A vector comprising a mutated *E. coli* araD gene, wherein said mutated *E. coli* araD gene comprises SEQ ID NO: 19, except that codon 8 of the *E. coli* araD gene has been mutated to encode a stop codon rather than a glutamine.

12. The vector of claim 11, wherein the cytidine at nucleic acid position 22 of SEQ ID NO: 19 is substituted with thymidine.

13. The vector of any one of claims 7-12, wherein said vector is an expression vector comprising:
(a) an isolated DNA sequence encoding a nuclear-anchoring protein operatively linked to a heterologous promoter, wherein said nuclear-anchoring protein is the E2 protein of Bovine Papilloma Virus type 1 (BPV), and (b) an isolated, multimerized DNA sequence forming a binding site for said nuclear-anchoring protein, wherein said binding site comprises multiple binding sites for the BPV E2 protein incorporated into the vector as a cluster, wherein said binding sites can be head-to-tail structures or can be included into said vector by spaced positioning, and wherein said vector lacks a papilloma virus origin of replication.

14. The vector of claim 13, further comprising a deletion in said multimerized DNA sequence.

15. The vector of claim 13, further comprising a mutation in the Shine-Dalgarno sequence of the mutated E. coli araD gene.

16. A selection system comprising an E. coli cell deficient of the E. coli araD gene into which a vector comprising an E. coli araD gene has been added as a selection marker, wherein said E. coli araD gene comprises SEQ ID NO: 1.

17. A selection system comprising an E. coli cell deficient of the E. coli araD gene into which a vector comprising an E. coli araD gene has been added as a selection marker, wherein said E. coli araD gene comprises SEQ ID NO: 18.

18. A selection system comprising an E. coli cell deficient of the E. coli araD gene into which a vector comprising an E. coli araD gene has been added as a selection marker, wherein said E. coli araD gene comprises SEQ ID NO: 19.

19. A selection system comprising an E. coli cell deficient of the E. coli araD gene into which a vector comprising a mutated E. coli araD gene has been added as a selection marker, wherein said mutated E. coli araD gene comprises SEQ ID NO: 1, except that codon 8 of the mutated E. coli araD gene has been mutated to encode a stop codon rather than a glutamine.

20. The selection system of claim 19, wherein the guanine at nucleic acid position 709 of SEQ ID NO: 1 is substituted with adenine.

21. A selection system comprising an E. coli cell deficient of the E. coli araD gene into which a vector comprising a mutated E. coli araD gene has been added as a selection marker, wherein said mutated E. coli araD gene comprises SEQ ID NO: 18, except that codon 8 of the mutated E. coli araD gene has been mutated to encode a stop codon rather than a glutamine.

22. The selection system of claim 21, wherein the cytidine at nucleic acid position 320 of SEQ ID NO: 18 is substituted with thymidine.

23. A selection system comprising an E. coli cell deficient of the E. coli araD gene into which a vector comprising a mutated E. coli araD gene has been added as a selection marker, wherein said mutated E. coli araD gene comprises SEQ ID NO: 19, except that codon 8 of the mutated E. coli araD gene has been mutated to encode a stop codon rather than a glutamine.

24. The selection system of claim 23, wherein the cytidine at nucleic acid position 22 of SEQ ID NO: 19 is substituted with thymidine.

25. A method of selecting cells transformed with a plasmid containing a nucleic acid sequence comprising an E. coli araD gene as a selection marker and a gene of interest, wherein said method comprises:
 (a) inserting said plasmid into an E. coli cell deficient of the E. coli araD gene; and
 (b) growing the cells in a growth medium containing arabinose;
 wherein said E. coli araD gene comprises SEQ ID NO: 1.

26. A method of selecting cells transformed with a plasmid containing a nucleic acid sequence comprising an E. coli araD gene as a selection marker and a gene of interest, wherein said method comprises:
 (a) inserting said plasmid into an E. coli cell deficient of the E. coli araD gene; and
 (b) growing the cells in a growth medium containing arabinose;
 wherein said E. coli araD gene comprises SEQ ID NO: 18.

27. A method of selecting cells transformed with a plasmid containing a nucleic acid sequence comprising an E. coli araD gene as a selection marker and a gene of interest, wherein said method comprises:
 (a) inserting said plasmid into an E. coli cell deficient of the E. coli araD gene; and
 (b) growing the cells in a growth medium containing arabinose;
 wherein said E. coli araD gene comprises SEQ ID NO: 19.

28. A method of selecting cells transformed with a plasmid containing a nucleic acid sequence comprising a mutated E. coli araD gene as a selection marker and a gene of interest, wherein said method comprises:
 (a) inserting said plasmid into an E. coli cell deficient of the E. coli araD gene; and
 (b) growing the cells in a growth medium containing arabinose;
 wherein said mutated E. coli araD gene comprises SEQ ID NO: 1, except that codon 8 of the mutated E. coli araD gene has been mutated to encode a stop codon rather than a glutamine.

29. The method of claim 28, wherein the guanine at nucleic acid position 709 of SEQ ID NO: 1 is substituted with adenine.

30. A method of selecting cells transformed with a plasmid containing a nucleic acid sequence comprising a mutated E. coli araD gene as a selection marker and a gene of interest, wherein said method comprises:
 (a) inserting said plasmid into an E. coli cell deficient of the E. coli araD gene; and
 (b) growing the cells in a growth medium containing arabinose;
 wherein said mutated E. coli araD gene comprises SEQ ID NO: 18, except that codon 8 of the mutated E. coli araD gene has been mutated to encode a stop codon rather than a glutamine.

31. The method of claim 30, wherein the cytidine at nucleic acid position 320 of SEQ ID NO: 18 is substituted with thymidine.

32. A method of selecting cells transformed with a plasmid containing a nucleic acid sequence comprising a mutated E. coli araD gene as a selection marker and a gene of interest, wherein said method comprises:
 (a) inserting said plasmid into an E. coli cell deficient of the E. coli araD gene; and
 (b) growing the cells in a growth medium containing arabinose;
 wherein said mutated E. coli araD gene comprises SEQ ID NO: 19, except that codon 8 of the mutated E. coli araD gene has been mutated to encode a stop codon rather than a glutamine.

33. The method of claim 32, wherein the cytidine at nucleic acid position 22 of SEQ ID NO: 19 is substituted with thymidine.

34. The selection system of any one of claims 16-24, wherein said E. coli cell deficient of the E. coli araD gene is an E. coli strain DH5 alpha, AG1, or JM109 cell deficient of the E. coli araD gene.

* * * * *

SEQUENCE LISTING

<160> NUMBER OF SEQ ID NOS: 29

<210> SEQ ID NO 1
<211> LENGTH: 780
<212> TYPE: DNA
<213> ORGANISM: Escherichia coli

<400> SEQUENCE: 1

```
gtttcgtttg attggctgtg gttttataca gtcattactg cccgtaatat gccttcgcgc      60
catgcttacg cagatagtgt ttatccagca gcgtttgctg catatccggt aactgcggcg     120
ctaactgacg gcagaatatc cccatataag cgacctcttc cagcacgatg gcgttatgca     180
ccgcatcttc ggcattttttg ccccatgcaa acgggccgtg ggaatggacc agaacgccgg     240
gcatttgcgc tgcatcgata ccctgttttt caaaggtttc tacgatgacg ttaccggttt     300
cccactcata ttcgccgttg atttctgcgt cggtcatttt gcgggtgcag ggaatggtgc     360
cgtagaaata gtcggcgtgg gtggtgccgg ttgctggaat cgactgaccc gcctgcgccc     420
agatggtggc gtggcgcgag tgcgtatgca caatgccgcc aatggagggg aatgcctgat     480
agagcagccg gtgagttggc gtgtcggagg agggcttttt cgtaccttca accacttcac     540
cggtttcgat gctaaccacg accatatcgt cagcggtcat gacgctgtaa tcgacgccgg     600
aaggtttgat cacaaagacg ccgcgctcgc gatcaacggc gctgacgttg ccccatgtga     660
gcgtgaccag gttgtgtttt ggcagcgcca ggttggcttc taatacctgg cgtttgagat     720
```

```
cttctaacat gttgactcct tcgtgccgga tgcgctttgc ttatccggcc tacaaaatcg    780
```

<210> SEQ ID NO 2
<211> LENGTH: 76
<212> TYPE: DNA
<213> ORGANISM: Artificial Sequence
<220> FEATURE:
<223> OTHER INFORMATION: Primer

<400> SEQUENCE: 2

```
cgccatggtt ctcatgtttg acagcttatc atcgataagc tttaatgcgg tagtttagca    60
cgaaggagtc aacatg                                                    76
```

<210> SEQ ID NO 3
<211> LENGTH: 64
<212> TYPE: DNA
<213> ORGANISM: Artificial Sequence
<220> FEATURE:
<223> OTHER INFORMATION: Primer

<400> SEQUENCE: 3

```
cgccatggac tagtaaaaaa aagcccgctc attaggcggg ctgtcattac tgcccgtaat    60
atgc                                                                 64
```

<210> SEQ ID NO 4
<211> LENGTH: 81
<212> TYPE: DNA
<213> ORGANISM: Artificial Sequence
<220> FEATURE:
<223> OTHER INFORMATION: Primer

<400> SEQUENCE: 4

```
cgccatggac tagttctcat gtttgacagc ttatcatcga taagctttaa tgcggtagtt    60
tagcacgaag gagtcaacat g                                              81
```

<210> SEQ ID NO 5
<211> LENGTH: 58
<212> TYPE: DNA
<213> ORGANISM: Artificial Sequence
<220> FEATURE:
<223> OTHER INFORMATION: Primer

<400> SEQUENCE: 5

```
cgccatggaa aaaaagccc gctcattagg cgggctgtca ttactgcccg taatatgc       58
```

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6

```
gccagggttt tcccagtcac ga                                             22
```

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7

```
gagcggataa caatttcaca cagg                                           24
```

```
<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
ccaactcacc ggctgctcta tc                                              22

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
aatgccgaag atgcggtgca taac                                            24

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
taactgcggc gctaactgac                                                 20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
ggttgctgga atcgactgac                                                 20

<210> SEQ ID NO 12
<211> LENGTH: 66
<212> TYPE: DNA
<213> ORGANISM: Artificial Sequence
<220> FEATURE:
<223> OTHER INFORMATION: Primer

<400> SEQUENCE: 12
ctcaaacgcc caggtattag aagccaacct ggcgctgcca aaacacgtgt aggctggagc     60
tgcttc                                                                66

<210> SEQ ID NO 13
<211> LENGTH: 60
<212> TYPE: DNA
<213> ORGANISM: Artificial Sequence
<220> FEATURE:
<223> OTHER INFORMATION: Primer

<400> SEQUENCE: 13
ggtttgatca caaagacgcc gcgctcgcga tcaacggcgc attccgggga tccgtcgacc     60

<210> SEQ ID NO 14
<211> LENGTH: 20
<212> TYPE: DNA
```

```
<213> ORGANISM: Artificial Sequence
<220> FEATURE:
<223> OTHER INFORMATION: Primer

<400> SEQUENCE: 14
cggcacgaag gagtcaacat                                                      20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
tgatagagca gccggtgagt                                                      20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
tcagatcctt ggcggcaaga                                                      20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
tgtaatcgac gccggaaggt                                                      20

<210> SEQ ID NO 18
<211> LENGTH: 1030
<212> TYPE: DNA
<213> ORGANISM: Artificial Sequence
<220> FEATURE:
<223> OTHER INFORMATION: 10E2BS-Promoter-RBS-araD-
      terminator

<400> SEQUENCE: 18
ggatccgacc ggcaacggta cagatccgac cggcaacggt acagatccga ccggcaacgg          60
tcagatccga ccggcaacgg tacagatccg accggcaacg gtacagatcc gaccggcaac         120
ggtacagatc cgaccggcaa cggtacagat ccgaccggca acggtacaga tccgaccggc         180
aacggtacag atccgaccgg caacggtaca gatcccccta gcgaattgac tagttctcat         240
gtttgacagc ttatcatcga taagctttaa tgcggtagtt tagcacgaag gagtcaacat         300
gttagaagat ctcaaacgcc aggtattaga agccaacctg gcgctgccaa acacaaacct         360
ggtcacgctc acatgggggca acgtcagcgc cgttgatcgc gagcgcggcg tctttgtgat         420
caaaccttcc ggcgtcgatt acagcgtcat gaccgctgac gatatggtcg tggttagcat         480
cgaaaccggt gaagtggttg aaggtacgaa aaagccctcc tccgacacgc caactcaccg         540
gctgctctat caggcattcc cctccattgg cggcattgtg catacgcact cgcgccacgc         600
caccatctgg gcgcaggcgg gtcagtcgat tccagcaacc ggcaccaccc acgccgacta         660
tttctacggc accattccct gcacccgcaa aatgaccgac gcagaaatca acggcgaata         720
```

| | |
|---|---:|
| tgagtgggaa accggtaacg tcatcgtaga aacctttgaa aaacagggta tcgatgcagc | 780 |
| gcaaatgccc ggcgttctgg tccattccca cggcccgttt gcatgggca aaaatgccga | 840 |
| agatgcggtg cataacgcca tcgtgctgga agaggtcgct tatatgggga tattctgccg | 900 |
| tcagttagcg ccgcagttac cggatatgca gcaaacgctg ctggataaac actatctgcg | 960 |
| taagcatggc gcgaaggcat attacgggca gtaatgacag cccgcctaat gagcgggctt | 1020 |
| tttttttccat | 1030 |

<210> SEQ ID NO 19
<211> LENGTH: 696
<212> TYPE: DNA
<213> ORGANISM: Escherichia coli

<400> SEQUENCE: 19

| | |
|---|---:|
| atgttagaag atctcaaacg ccaggtatta gaagccaacc tggcgctgcc aaaacacaac | 60 |
| ctggtcacgc tcacatgggg caacgtcagc gccgttgatc gcgagcgcgg cgtctttgtg | 120 |
| atcaaacctt ccggcgtcga ttacagcgtc atgaccgctg acgatatggt cgtggttagc | 180 |
| atcgaaaccg gtgaagtggt tgaaggtacg aaaaagcccct cctccgacac gccaactcac | 240 |
| cggctgctct atcaggcatt cccctccatt ggcggcattg tgcatacgca ctcgcgccac | 300 |
| gccaccatct gggcgcaggc gggtcagtcg attccagcaa ccggcaccac ccacgccgac | 360 |
| tatttctacg gcaccattcc ctgcacccgc aaaatgaccg acgcagaaat caacggcgaa | 420 |
| tatgagtggg aaaccggtaa cgtcatcgta gaaacctttg aaaaacaggg tatcgatgca | 480 |
| gcgcaaatgc ccggcgttct ggtccattcc cacggcccgt ttgcatgggg caaaaatgcc | 540 |
| gaagatgcgg tgcataacgc catcgtgctg gaagaggtcg cttatatggg gatattctgc | 600 |
| cgtcagttag cgccgcagtt accggatatg cagcaaacgc tgctggataa acactatctg | 660 |
| cgtaagcatg gcgcgaaggc atattacggg cagtaa | 696 |

<210> SEQ ID NO 20
<211> LENGTH: 687
<212> TYPE: DNA
<213> ORGANISM: Escherichia coli

<400> SEQUENCE: 20

| | |
|---|---:|
| atgcaaaagc taaacagca ggtatttgaa gccaacatgg agctgccgcg ctacgggctg | 60 |
| gtgacctta cctggggcaa cgtcagcgct atcgaccgcg aacgcgggct ggtggtgatc | 120 |
| aagcccagcg gcgttgccta cgaaaccatg aaagcggccg atatggtggt ggttgatatg | 180 |
| agcggcaagg tggtggaagg ggagtatcgc ccatcttccg cactgcgac gcatctcgaa | 240 |
| ctctaccgtc gttacccgtc gcttggtggc attgtccata cccactccac tcatgccacc | 300 |
| gcatgggcgc aggcggggct ggcgatcccg gcgttaggca ccacgcacgc cgactacttc | 360 |
| tttggcgaca ttccgtgtac gcgcgggtta agcgaagaag aggtgcaggg cgagtatgaa | 420 |
| ctgaacaccg gcaaagtgat tatcgaaacg ctgggcaacg ccgagccgct gcatacgccg | 480 |
| ggaattgtgg tgtatcagca cgggccgttc gcctggggga agatgctca cgatgcggtg | 540 |
| cataacgcgg tggtgatgga agaagtggcg aaaatggcgt ggattgcccg cggcattaac | 600 |
| ccacaactca atcacatcga cagcttcctg atgaataaac acttcatgcg taaacacggt | 660 |
| cctaacgctt attacgggca gaagtag | 687 |

<210> SEQ ID NO 21
<211> LENGTH: 65

<210> SEQ ID NO 21
<211> LENGTH: 65
<212> TYPE: DNA
<213> ORGANISM: Artificial Sequence
<220> FEATURE:
<223> OTHER INFORMATION: Primer

<400> SEQUENCE: 21
cagcaggtat ttgaagccaa catggagctg ccgcgctacg ggctggtgta ggctggagct    60
gcttc                                                                65

<210> SEQ ID NO 22
<211> LENGTH: 66
<212> TYPE: DNA
<213> ORGANISM: Artificial Sequence
<220> FEATURE:
<223> OTHER INFORMATION: Primer

<400> SEQUENCE: 22
aaacggctgc ggaattagac cagttatctc ccgaggaagg aaattaattc cggggatccg    60
tcgacc                                                               66

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
aaacggctgc ggaattagac c                                              21

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
gccgtacctg attgagatgt ggag                                           24

<210> SEQ ID NO 25
<211> LENGTH: 696
<212> TYPE: DNA
<213> ORGANISM: Escherichia coli

<400> SEQUENCE: 25
atgttagagc aactgaaagc cgacgtgctg cggcgaatc tggcgcttcc cgctcaccat     60
ctggtgacgt tcacctgggg caatgtcagc gcggtagacg aaacgcggca atggatggta   120
atcaaacctt ccggcgtcga gtacgacgtg atgaccgccg acgatatggt ggtggttgag   180
atagccagcg gtaaggtggt ggaaggcagc aaaaaaccct cttccgatac accaacgcat   240
ctggcgctct accgtcgcta tgccgaaatt ggcggtattg tgcatacccca ctcgcgccac   300 gccaccatct ggtcacaggc cgggctggat ctccccgcct ggggcaccac ccacgccgat   360 tattttacg gtgccatccc ctgcacgcga cagatgaccg cagaggagat taacggcgaa   420
tatgaatatc agaccggcga agtgatcatt gaaaccttcg aagaacgtgg caggagtccg   480
gcacaaatcc cggcggtgct ggtgcattct cacggcccgt tcgcatgggg taaaaacgcc   540
gccgatgccg tgcataacgc cgtagtactc gaagaatgcg cctatatggg tctattctcg   600
cgccagcttg cgccgcagct ccctgcgatg caaaacgaac tgctggataa gcactacctg   660

-continued

```
cgtaagcatg gggccaatgc ctattacggg cagtaa                              696
```

<210> SEQ ID NO 26
<211> LENGTH: 67
<212> TYPE: DNA
<213> ORGANISM: Artificial Sequence
<220> FEATURE:
<223> OTHER INFORMATION: Primer

<400> SEQUENCE: 26

```
cgttacagca aggaacatat caattcgtag tgccggggcg atgaagaatt ccggggatcc    60
gtcgacc                                                              67
```

<210> SEQ ID NO 27
<211> LENGTH: 65
<212> TYPE: DNA
<213> ORGANISM: Artificial Sequence
<220> FEATURE:
<223> OTHER INFORMATION: Primer

<400> SEQUENCE: 27

```
gcaggaggct ggatttatat gttagagcaa ctgaaagccg acgtggtgta ggctggagct    60
gcttc                                                                65
```

<210> SEQ ID NO 28
<211> LENGTH: 24
<212> TYPE: DNA
<213> ORGANISM: Artificial Sequence
<220> FEATURE:
<223> OTHER INFORMATION: Primer

<400> SEQUENCE: 28

```
cggcgttaca gcaaggaaca tatc                                           24
```

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29

```
attgaagcgc gtatgcagga gg                                             22
```